(12) United States Patent
Allen et al.

(10) Patent No.: US 9,974,138 B2
(45) Date of Patent: May 15, 2018

(54) MULTI-CHANNEL LAMP SYSTEM AND METHOD WITH MIXED SPECTRUM

(71) Applicant: GE LIGHTING SOLUTIONS, LLC, East Cleveland, OH (US)

(72) Inventors: Gary Robert Allen, Chesterland, OH (US); Ashfaqul I. Chowdhury, Broadview Heights, OH (US); David C. Dudik, Shaker Heights, OH (US); Kevin James Vick, Cleveland Heights, OH (US); Thomas J. Boyle, Lyndhurst, OH (US)

(73) Assignee: GE LIGHTING SOLUTIONS, LLC, East Cleveland, OH (US)

( * ) Notice: Subject to any disclaimer, the term of this patent is extended or adjusted under 35 U.S.C. 154(b) by 0 days. days.

(21) Appl. No.: 14/757,957

(22) Filed: Dec. 24, 2015

(65) Prior Publication Data

US 2016/0316527 A1 Oct. 27, 2016

Related U.S. Application Data

(60) Provisional application No. 62/150,800, filed on Apr. 21, 2015.

(51) Int. Cl.
| | | |
|---|---|---|
| *H05B 33/08* | (2006.01) | |
| *A61N 5/06* | (2006.01) | |
| *F21V 23/04* | (2006.01) | |
| *H05B 37/02* | (2006.01) | |
| *F21Y 101/00* | (2016.01) | |
| *F21Y 115/10* | (2016.01) | |

(52) U.S. Cl.
CPC ......... *H05B 33/086* (2013.01); *A61N 5/0618* (2013.01); *F21V 23/04* (2013.01); *H05B 37/0281* (2013.01); *F21Y 2101/00* (2013.01); *F21Y 2115/10* (2016.08)

(58) Field of Classification Search
CPC .................................................. H05B 33/0857
USPC ................................................. 362/231, 235
See application file for complete search history.

(56) References Cited

U.S. PATENT DOCUMENTS

| | | |
|---|---|---|
| 5,343,316 A | 8/1994 | Morimoto et al. |
| 5,998,925 A | 12/1999 | Shimizu et al. |

(Continued)

FOREIGN PATENT DOCUMENTS

| | | |
|---|---|---|
| WO | 2013030727 | 3/2013 |
| WO | 2013030731 | 4/2013 |

(Continued)

OTHER PUBLICATIONS

Chemical Book, Potassium Fluorosilicate, Web Page, Jul. 4, 2013.*

(Continued)

*Primary Examiner* — Elmito Breval
*Assistant Examiner* — Keith Delahoussaye
(74) *Attorney, Agent, or Firm* — Peter T. DiMauro; GE Global Patent Operation

(57) ABSTRACT

Composite light sources and methods use a low-blue component light source emitting first substantially white light and a high-blue component light source emitting second substantially white light. The second substantially white light has a greater correlated color temperature than the first substantially white light. The first and second substantially white light combine to provide substantially intermediate warm-white light.

14 Claims, 28 Drawing Sheets

(56) References Cited

U.S. PATENT DOCUMENTS

| | | | |
|---|---|---|---|
| 6,016,038 A | 1/2000 | Mueller | |
| 6,150,774 A | 11/2000 | Mueller | |
| 6,788,011 B2 | 9/2004 | Mueller | |
| 6,806,659 B1 | 10/2004 | Mueller | |
| 7,014,336 B1 | 3/2006 | Ducharme | |
| 7,038,399 B2 | 5/2006 | Lys | |
| 7,242,152 B2 | 7/2007 | Dowling | |
| 7,248,239 B2 | 7/2007 | Dowling | |
| 7,253,566 B2 | 8/2007 | Lys | |
| 7,255,457 B2 | 8/2007 | Ducharme | |
| 7,256,554 B2 | 8/2007 | Lys | |
| 7,274,160 B2 | 9/2007 | Mueller | |
| 7,300,192 B2 | 11/2007 | Mueller | |
| 7,303,300 B2 | 12/2007 | Dowling | |
| 7,308,296 B2 | 12/2007 | Lys | |
| 7,309,965 B2 | 12/2007 | Dowling | |
| 7,344,279 B2 | 3/2008 | Mueller | |
| 7,348,736 B2 | 3/2008 | Piepgras | |
| 7,350,936 B2 | 4/2008 | Ducharme | |
| 7,352,138 B2 | 4/2008 | Lys | |
| 7,352,339 B2 | 4/2008 | Morgan | |
| 7,353,071 B2 | 4/2008 | Blackwell | |
| 7,354,172 B2 | 4/2008 | Chemel | |
| 7,358,679 B2 | 4/2008 | Lys | |
| 7,358,706 B2 | 4/2008 | Lys | |
| 7,358,929 B2 | 4/2008 | Mueller | |
| 7,364,488 B2 | 4/2008 | Mueller | |
| 7,385,359 B2 | 6/2008 | Dowling | |
| 7,387,405 B2 | 6/2008 | Ducharme | |
| 7,427,840 B2 | 9/2008 | Morgan | |
| 7,449,847 B2 | 11/2008 | Schanberger | |
| 7,453,217 B2 | 11/2008 | Lys | |
| 7,459,864 B2 | 12/2008 | Lys | |
| 7,462,997 B2 | 12/2008 | Mueller | |
| 7,477,009 B2 | 1/2009 | Nagatomi et al. | |
| 7,482,565 B2 | 1/2009 | Morgan | |
| 7,482,764 B2 | 1/2009 | Morgan | |
| 7,495,671 B2 | 2/2009 | Chemel | |
| 7,502,034 B2 | 3/2009 | Chemel | |
| 7,511,437 B2 | 3/2009 | Lys | |
| 7,515,128 B2 | 4/2009 | Dowling | |
| 7,520,634 B2 | 4/2009 | Ducharme | |
| 7,525,254 B2 | 4/2009 | Lys | |
| 7,542,257 B2 | 6/2009 | McCormick | |
| 7,543,951 B2 | 6/2009 | Koerner | |
| 7,543,956 B2 | 6/2009 | Piepgras | |
| 7,550,931 B2 | 6/2009 | Lys | |
| 7,550,935 B2 | 6/2009 | Lys | |
| 7,557,521 B2 | 7/2009 | Lys | |
| 7,572,028 B2 | 8/2009 | Mueller | |
| 7,598,681 B2 | 10/2009 | Lys | |
| 7,598,684 B2 | 10/2009 | Lys | |
| 7,598,686 B2 | 10/2009 | Lys | |
| 7,619,370 B2 | 11/2009 | Chemel | |
| 7,642,730 B2 | 1/2010 | Dowling | |
| 7,646,029 B2 | 1/2010 | Mueller | |
| 7,652,436 B2 | 1/2010 | Dowling | |
| 7,658,506 B2 | 2/2010 | Dowling | |
| 7,659,673 B2 | 2/2010 | Lys | |
| 7,659,674 B2 | 2/2010 | Mueller | |
| 7,679,281 B2 | 3/2010 | Kim | |
| 7,703,951 B2 | 4/2010 | Piepgras | |
| 8,018,151 B2 | 9/2011 | Chung | |
| 8,025,421 B2 | 9/2011 | Ku | |
| 8,133,461 B2 | 3/2012 | Tao et al. | |
| 8,159,125 B2 | 4/2012 | Miao | |
| 8,203,260 B2 | 6/2012 | Li | |
| 8,217,404 B2 | 7/2012 | Wu | |
| 8,292,486 B2 | 10/2012 | Wang | |
| 8,330,394 B2 | 12/2012 | Custodis | |
| 8,348,457 B2 | 1/2013 | Kadotani | |
| 8,410,727 B2 | 4/2013 | Mizuno | |
| 8,436,549 B2 | 5/2013 | Hasnain | |
| 8,449,129 B2 | 5/2013 | Harbers | |
| 8,581,520 B1 | 11/2013 | Wray | |
| 8,648,523 B2 | 2/2014 | Murazaki et al. | |
| 8,698,425 B2 | 4/2014 | Mizuno | |
| 8,779,687 B2 | 7/2014 | Harbers | |
| 8,816,590 B2 | 8/2014 | Kuo | |
| 8,841,856 B1 | 9/2014 | Beasley | |
| 8,841,864 B2 | 9/2014 | Maxik | |
| 8,952,627 B2 | 2/2015 | Tomiyama | |
| 2007/0258240 A1 | 11/2007 | Ducharme | |
| 2008/0265207 A1 | 10/2008 | Konrad et al. | |
| 2009/0033246 A1 | 2/2009 | Tsai et al. | |
| 2009/0184669 A1 | 7/2009 | Tsai et al. | |
| 2009/0303694 A1* | 12/2009 | Roth | C09K 11/7734 362/84 |
| 2010/0096998 A1 | 4/2010 | Beers | |
| 2010/0171441 A1 | 7/2010 | Schlangen et al. | |
| 2011/0062868 A1 | 3/2011 | Domagala | |
| 2011/0084614 A1 | 4/2011 | Eisele et al. | |
| 2011/0089866 A1 | 4/2011 | Trotter | |
| 2011/0205727 A1 | 8/2011 | Kim | |
| 2011/0285295 A1 | 11/2011 | Son | |
| 2012/0008318 A1 | 1/2012 | Ishiwata | |
| 2012/0008326 A1 | 1/2012 | Jou | |
| 2012/0037933 A1 | 2/2012 | Roth et al. | |
| 2012/0038291 A1 | 2/2012 | Hasnain | |
| 2012/0095534 A1 | 2/2012 | Schlangen | |
| 2012/0098411 A1 | 4/2012 | Toth et al. | |
| 2012/0161170 A1* | 6/2012 | Dubuc | A01G 7/045 257/89 |
| 2013/0020929 A1 | 1/2013 | Van De Ven et al. | |
| 2013/0076262 A1 | 3/2013 | Noguchi | |
| 2013/0114242 A1 | 5/2013 | Pickard et al. | |
| 2013/0128603 A1 | 5/2013 | Chen | |
| 2013/0134888 A1 | 5/2013 | Grajcar | |
| 2013/0140590 A1 | 6/2013 | Hsieh | |
| 2013/0271033 A1 | 10/2013 | Lou | |
| 2013/0293152 A1 | 11/2013 | Barroso | |
| 2014/0103813 A1 | 4/2014 | Moss | |
| 2014/0139138 A1 | 5/2014 | Liu | |
| 2014/0159084 A1 | 6/2014 | Castillo et al. | |
| 2014/0159584 A1 | 6/2014 | Grajcar | |
| 2014/0160719 A1 | 6/2014 | Van Boven et al. | |
| 2014/0160720 A1 | 6/2014 | Van Boven et al. | |
| 2014/0168965 A1 | 6/2014 | Moon | |
| 2014/0197759 A1 | 7/2014 | Wray | |
| 2014/0228914 A1 | 8/2014 | Van de Ven et al. | |
| 2014/0232292 A1 | 8/2014 | Adler | |
| 2014/0288359 A1 | 9/2014 | Baaijens | |
| 2014/0307466 A1 | 10/2014 | Hikmet | |
| 2015/0008835 A1 | 1/2015 | Sugiura | |
| 2015/0048399 A1* | 2/2015 | Weiler | H01L 33/502 257/98 |
| 2015/0062892 A1* | 3/2015 | Krames | H05B 37/0281 362/231 |

FOREIGN PATENT DOCUMENTS

| | | |
|---|---|---|
| WO | 2014064582 | 5/2014 |
| WO | 2014111821 | 7/2014 |
| WO | 2014119313 | 8/2014 |
| WO | 2014177409 | 11/2014 |
| WO | 2015035425 A1 | 3/2015 |
| WO | 2015040036 | 3/2015 |

OTHER PUBLICATIONS

Zhang, M. et al, Color Temperature Tunable White-Light LED Cluster with Extrahigh Color Rendering Index, Jan. 23, 2014, Hindawi Publishing Corporation, vol. 2014.*

Rea et al., "Circadian light", Journal of Circadian Rhythms, Volume No. 8, Issue No. 2, pp. 1-10, 2010.

Ohno, "Calculation of CCT and Duv and Practical Conversion Formulae", CORM 2011 Conference, Gaithersburg, MD, pp. 1-28, May 3-5, 2011.

Ohno et al., "Light Spectrum and Color Quality", Department of Energy, Solid State Lighting R&D Workshop, pp. 1-29, Jan. 29-31, 2013.

(56) References Cited

OTHER PUBLICATIONS

Rea et al., "White Lighting", COLOR research and application, Volume No. 38, pp-82-92, Apr. 2013.

Ohno et al., "Vision Experiment on White Light Chromaticity for Lighting", Duv levels Perceived Most Natural, pp. 1-39, Nov. 7-8, 2013.

Rea et al., "A Working Threshold for Acute Nocturnal Melatonin Suppression from "White" Light Sources used in Architectural Applications", Carcinogenesis & Mutagene, Volume No. 4, Issue No. 3, pp. 1-6, 2013.

Ohno, "NIST Research on Color Quality of SSL Sources", DOE Solid State Lighting R&D Workshop, pp. 1-28, Jan. 28-30, 2014.

Carey, "LED Phosphor IP Trends and Licensing," available at http://www.ecnmag.com/articles/2014/05/led-phosphor-ip-trends-and-licensing, pp. 1-8, May 21, 2014.

International Search Report and Written Opinion issued in connection with corresponding PCT Application No. PCT/US2014/054868 dated Dec. 16, 2014.

Ohno, "Color Preference-based LED lighting", SPARC International Lighting Events 2015, pp. 1-42, May 27-29, 2015.

GE Align, available at http://www.gelighting.com/LightingWeb/align/index.jsp, Aug. 4, 2015.

Ohno et al., "Vision Experiment II on White Light Chromaticity for Lighting", Duv range perceived most natural, pp. 1-31, Oct. 19-20, 2015.

International Search Report and Written Opinion issued in connection with corresponding PCT Application No. PCT/US2016/026871 dated Jul. 11, 2016.

* cited by examiner

MULTI-CHANNEL LAMP SYSTEM AND METHOD WITH MIXED SPECTRUM

CROSS-REFERENCE TO RELATED APPLICATIONS

This application claims priority to U.S. Provisional Application No. 62/150,800, which was filed on 21 Apr. 2015, and the entire disclosure of which is incorporated herein by reference.

FIELD

Embodiments of the subject matter disclosed herein relate to lighting systems.

BACKGROUND

It is known that light having a relatively high amount of blue light may correlate with melatonin suppression in humans and other mammals, and that melatonin is a key hormone involved in the entrainment (synchronization) of the circadian rhythms of physiological functions including sleep timing and many others. Therefore, a low-blue, low correlated color temperature (CCT) (e.g., 2000 K) spectrum at low lux levels encourages melatonin production and helps a user of a light source embodying such spectrum to promote sleep. A high-blue, high CCT (e.g. 7000 K) spectrum at high lux levels generally suppresses melatonin production, and may assist a user of a light source that embodies such spectrum to awaken in the morning and feel alert during the day. This relatively new application of lighting is known as Circadian Lighting, or as a subset of Human-centric Lighting.

Some light-emitting diode (LED)-based lamps which may pertain to the effect of light on human melatonin production or suppression, are known. United States Patent Application Publication No. 2015/0062892 describes a light source formed to include a first LED emission (e.g., one or more LEDs emitting a first spectrum) and a second LED emission (e.g., one or more LEDs emitting a second spectrum), where the first and second LED emissions are combined in a first ratio and in a second ratio such that while changing from the first ratio to the second ratio the relative circadian stimulation is varied while maintaining a color rendering index above 80.

United States Patent Application Publication No. 2012/0008326 describes a lighting device that includes a light-emitting device being able to emit a visible light and a light-filtering device being close to the light-emitting device. When the light-emitting device emits the visible light, the light-filtering device is able to filter a blue light component of the visible light so as to reduce the blue light component within the visible light emitted by the light-emitting device, thereby reducing the effects on suppressing the melatonin caused by the visible light.

United States Patent Application Publication No. 2014/0228914 describes solid-state light-emitting devices that include multiple LED components providing adjustable melatonin suppression effects. Multiple LED components may be operated simultaneously according to different operating modes according to which their combined output provides the same or similar chromaticity, but provide melatonin suppressing effects that differ by at least a predetermined threshold amount between the different operating modes.

BRIEF DESCRIPTION

In one embodiment, a composite light source includes a low-blue component light source emitting first substantially white light and a high-blue component light source emitting second substantially white light and an optical system to combine and mix the light from the low-blue and high-blue light sources. The second substantially white light has a greater correlated color temperature than the first substantially white light. The first and second substantially white light are combined and mixed in the optical system to provide substantially white light having an intermediate correlated color temperature.

In another embodiment, a method (e.g., for generating light) includes emitting first substantially white light from a low-blue component light source of a composite light source during a first time of day and emitting second substantially white light from a high-blue component light source during a different, second time of day, [not to be confused with rapid switching of light sources, at a rate faster than the eye response] where the second substantially white light has a greater correlated color temperature than the first substantially white light.

In another embodiment, a composite light source includes a low-blue component light source emitting first substantially white light having a correlated color temperature (CCT) of no greater than about 2500 K, such as within 10%, 5%, 3%, or 1%, (or no greater than another value, such as about 2200 K or about 2000 K), a high-blue component light source emitting second substantially white light having a CCT of at least about 3200 K (or at least about 5000 K or at least about 6500 K), a control unit to control which of the low-blue component light source and the high-blue component light source is activated to emit the respective first substantially white light or the second substantially white light, and an optical system through which both the first substantially white light and the second substantially white light is emitted.

In another embodiment, a composite light source includes a low-blue component light source emitting first substantially white light having a correlated color temperature (CCT) of no greater than about 2500 K (or no greater than another value, such as about 2200 K or about 2000 K), a high-blue component light source emitting second substantially white light having a CCT of at least about 3200 K (or at least about 5000 K or at least about 6500 K), an optical system to combine and mix the light from the low-blue and high-blue light sources, and a control unit to control the amount of emission from the low-blue component light source and the high-blue component light source in order to emit either the respective first substantially white light or the second substantially white light or substantially white light having an intermediate CCT.

BRIEF DESCRIPTION OF THE DRAWINGS

The subject matter described herein will be better understood from reading the following description of non-limiting embodiments, with reference to the attached drawings, wherein below.

DETAILED DESCRIPTION

Figure 1A:
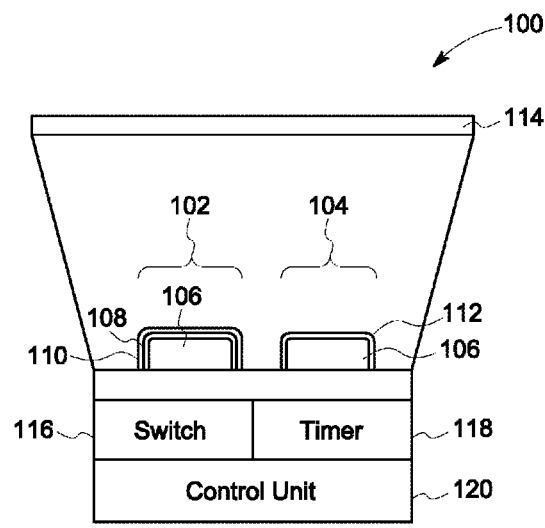
FIG. 1a illustrates one embodiment of a multi-channel lamp system that produces a mixed spectrum.

In some embodiments, a composite light source is provided that can be generated by the combination of the respective spectra of two or more component light sources. The first component light source may emit a "low-blue" light with a relatively low CCT, and the second component light source may emit a "high-blue" light with a relatively high CCT. Herein a low-blue light source is represented by a SPD distribution having a CCT in the range of about 1500 K to about 2500 K, but optionally as low as about 1000 K, that may be capable of limiting melatonin suppression so that a user can employ it at night. Herein a high-blue light source is represented by a SPD distribution having a CCT in the range of about 3200 K to about 6500 K, but optionally as high as about 10,000 K, as high as about 15,000 K, or an even larger value, that may be capable of suppressing melatonin production so that a user can employ it in the morning, or throughout the day.

In the emerging applications of Circadian Lighting, the terms "low-blue light" and "high-blue light" refer to the flux of melatonin-suppressing light incident at the cornea of the eye of the human subject. The flux of melatonin-suppressing light has been quantified in the 2010 publication Rea et al., Journal of Circadian Rhythms 2010, 8:2 (2010 Rea). Recommended permissible limits pertaining to low-blue and high-blue light have only recently appeared in the scientific literature, e.g. in 2013 Rea M S, Figueiro M G, "A Working Threshold for Acute Nocturnal Melatonin Suppression from "White" Light Sources used in Architectural Applications", J Carcinogene Mutagene 4: 150 (2013 Rea). (There are no lighting standards developed yet related to melatonin suppression.) Therein it is proposed that "the hypothesized working threshold for acute nocturnal melatonin suppression be 30-minute exposure to 30 lux at the cornea (i.e., a low-blue light threshold) from "white" light sources that might be used in architectural applications. These values represent a conservative estimate of dose, recognizing that the empirical results of the present studies and the traditional probability of a Type I error (i.e., $\alpha$<0.05), a one-hour exposure to 200 lux from the selected "warm white" light source would be the lowest lighting condition that could reliably suppress nocturnal melatonin synthesis. (i.e., a high-blue light threshold)". There are scientific publications that may define the action spectrum for circadian lumens differently from that shown as 160 in FIG. 1b; and that may define a method for quantifying "circadian lux" differently; and that may propose different threshold values for low-blue and high-blue light sources, but those differences would not substantially alter the elements of this invention.

Because a quantitative definition of a "low-blue" or "high-blue" light source, as in 2013 Rea, involves lux (lumens/m$^2$) incident on the cornea of the eye, these terms depend on the distance between the light source and the observer, as well as the reflective characteristics of the observer's environment. Therefore, it is impractical to quantitatively define the limits of a "low-blue" or "high-blue" light source in terms of circadian lux ($CL_A$) or photopic lux, as proposed in 2013 Rea, without reference to the observer's environment, distance from, and orientation to, the light source. Instead, we herein define "low-blue" and "high-blue" only in reference to the SPD of the light source, without regard to the intensity of the light source at the cornea of the observer.

The ratio of $CL_A$ to photopic lux is defined in 2010 Rea to be identically 1.0 for a "CIE standard illuminant A" (a blackbody radiator at a color temperature of 2856 K), similar in relative SPD to an incandescent lamp. Therefore, we may define a "low-blue" light source herein as having a ratio of $CL_A$:photopic lux less than 1.0, and more preferably less than about 0.8 or less than about 0.6, and a "high-blue" light source as having a ratio of $CL_A$:photopic lux greater than 1.0, and more preferably greater than about 1.2 or greater than about 1.4. In other words, we define "low-blue" and "high-blue" light sources herein as light sources providing "substantially less" and "substantially more" circadian lux at the cornea of the observer than a "CIE standard illuminant A" light source (e.g. an incandescent or warm-white LED light source) of the same photopic lux would provide. Since our definitions of low-blue and high-blue are independent of the photopic lux level, then the difference between low-blue and high-blue light sources, as defined herein, is determined only by the relative amount of "blue light" in the respective spectral power distributions. "Blue light" is defined herein as the portion of the SPD of the light source that is emitted within the range of the action spectrum for circadian lumens 160 in FIG. 1b, i.e., it is the circadian lumen flux of a light source, given by the integral over the visible spectrum (from 380 to 760 nm) of the action spectrum 160, or a similar action spectrum, for circadian lumens with the SPD of the light source.

The composite light source may be a combination of the spectra of the two component light sources, where the combination of the two spectra, providing a color point along a tie line between the color points of the respective component light sources, produces an intermediate white emission (e.g., a warm-white emission, such as in the range of about 2500 K to about 3200 K) near the white body locus, below the blackbody locus, with enhanced color preference. In some embodiments, the first and/or the second component light source comprises a narrow band red-emitting source (such as a red LED, a quantum dot emitter, an emerging-technology narrow red emitter such as a red phosphor having width narrower than the conventional red nitride phosphor, or a manganese-doped hexafluorometallate phosphor, e.g., potassium fluoro-silicate or PFS), to allow for color enhancement in various settings. The narrow band red emitter should have a full-width at half-maximum of less than about 60 nm, or more preferred less than about 30 nm. The composite light source may be employed for general illumination, or as a backlight for a display, or for other purposes.

In one embodiment, the narrow red emitter includes a phosphor such as PFS. The use of PFS instead of other narrow red emitters can provide one or more benefits, such as increased thermal stability, lower cost, and/or simplified control of the light sources. The red LED is thermally less stable and more expensive than the blue LED driver of a PFS red emitter. The emerging-technology red emitters available today are not nearly as narrow as the PFS phosphor, so that the full advantages of reduced near-IR emission and enhanced saturation of red objects are not provided by those phosphors. The quantum dots may have increased costs (e.g., due to the Restriction of Hazardous Substances directive and the presence of cadmium in quantum dots).

According to some embodiments described herein, the combination of a "low-blue" spectrum with a "high-blue" spectrum may permit the attainment of any color point along a tie line between the individual color points. For an intermediate or warm-white spectrum (e.g. about 2500 K to about 3200 K), the tie line for the combined spectrum may be located proximate to a "white body" line, or a "color-preference line". The "White Line" (also known as "white body locus" or "white body line") may be understood by reference to the following publication: "White Lighting," Color Research & Application, volume 38, #2, pp. 82-92 (2013), authors M. S. Rea & J. P. Freyssinier (henceforth, the "2013 Freyssinier reference"). The "color-preference line" may be understood by reference to the following publication: "Color Preference-based LED Lighting", SPARC International Lighting Events 2015 May 27-29, 2015, author Yoshi Ohno (henceforth, the "2015 Ohno reference"). If a narrow-band red-emitting source is used in the low-blue light source component and/or the high-blue light source component, this may allow for additional color enhancement and increased color quality metrics, such as CRI (Color Rendering Index), $R_9$ (special color rendering index of a standard saturated red), GAI (Gamut Area Index), and/or LPI (Lighting Preference Index, as described in published International Application WO-2015-035425). The International Application WO-2015-035425 discloses one definition for the LPI metric, and this published patent application is incorporated herein by reference. Spectral efficacy may also be increased by use of a narrow-band red-emitting source by eliminating the inefficient emission beyond about 640 nm that is typical of conventional broad red phosphors.

Typically, the composite light source of embodiments of this disclosure may function as a light source that works as a low-blue "night lamp," a high-blue "morning lamp," and a warm-white "enhanced color lamp," all in a single embodiment.

FIG. 1a illustrates one embodiment of a multi-channel lamp system 100 that produces a mixed spectrum. The system 100 optionally may be referred to as a composite light source. The system 100 includes plural different light sources 102, 104 that produce different spectra of light. The light sources 102, 104 can represent light emitting diodes (LEDs), organic light emitting diodes (OLEDs), laser diodes (LDs), or other types of devices that generate light. The light source 102 can be a low-blue light source and the light source 104 can represent a high-blue light source. Each of the light sources 102, 104 can generate white or substantially white light, but having different correlated color temperatures (CCT). For example, the light generated by the light source 102 may have a lower CCT than the light generated by the light source 104. The system 100 may operate by having different light sources 102 or 104 generating light at different times (without the other light source 104 or 102 concurrently generating light) and/or by the light sources 102, 104 generating light at the same time to generate substantially intermediate or warm-white light (e.g., light having a CCT of about 2700 to about 3000 K or another value). The term "about" can indicate that the CCT may be within a designated range of the stated value, such as within 10%, 5%, 3%, or 1%.

In one aspect, the light source 102 may generate light having a CCT of no greater than about 2500 K. The light generated by the light source 102 may have a CCT as low as about 1500 K to 2000 K, or even as low as about 1000 K, in one embodiment. The light source 104 may generate light having a CCT of at least about 3200 K. The light generated by the light source 104 may have a CCT as great as 10,000 K to 15,000 K, or higher, in one embodiment. One example of the light source 102 is the GE ALIGN PM light source with CCT about 2000 K, but the light source 102 can optionally include any light source that emits light that is substantially white and/or light having a CCT of less than about 2500 K (e.g., at least about 1500 K and no more than about 2500 K, or even as low as about 1000 K). One example of the light source 104 is the GE ALIGN AM light source with CCT about 7000 K, but the light source 104 can optionally include any light source that emits light that is substantially white and/or light having a CCT of greater than about 3200 K (e.g., as high as about 6500 K and or even about 15,000 K, or higher).

Exposure of the human body to the low amount of blue light in the light generated by the light source 102 can limit melatonin suppression in the body and help to regulate sleep cycle/circadian rhythm, particularly at night to fall asleep. For example, the body may be able to more easily generate melatonin when exposed to the low-blue light generated by the light source 102. Exposure to the greater amount of blue light in the light generated by the light source 104 can suppress melatonin generation in the body and help to make the body more alert and awake relative to exposure to the low-blue light of the light source 102.

In one embodiment, the light source 102 includes one or more blue LEDs 106 having phosphors 108, 110 disposed thereon. The phosphors 108, 110 may represent coatings or covers on the LED 106 that convert or partially convert the blue light generated by the LED 106. For example, the phosphor 108 may represent a yellow phosphor coating (e.g., a coating formed from yttrium aluminum garnet, or YAG) that partially converts the blue light generated by the LED 106 to yellow light for mixing with some transmitted blue light.

The phosphor 110 can represent a red-emitting phosphor coating. This coating can be formed from a narrow red emitter, such as PFS or $K_2[SiF_6]:Mn^{4+}$. Alternatively, the phosphor 110 may be formed from another material. Alternatively, the phosphor 110 can represent a combination of red-emitting phosphor coatings. For example, the phosphor 110 can include a broad-band red-emitting nitride phosphor (such as a phosphor with the general formula $CaAlSiN_3$:$Eu^{2+}$) and a narrow-band red-emitting phosphor.

In one embodiment, the phosphor 110 can represent a combination of red-emitting phosphor coatings. For example, the phosphor 110 can include a broad-band red-emitting nitride phosphor and a narrow-band red-emitting phosphor. In one embodiment, the phosphor 110 is formed by the broad-band red-emitting nitride phosphor with one or more percentages of the broad-band phosphor being replaced by the narrow-band red-emitting phosphor. In various embodiments, the following quantities of the broad-band red-emitting nitride phosphor in the phosphor 110 may be replaced by the narrow-band red-emitting phosphor: 0% (where the phosphor 110 is the broad-band red-emitting nitride phosphor only), 25%, 50%, and 100% (where the phosphor 110 is the narrow-band red-emitting phosphor only), or any quantity between 0% and 100%. The percentages of replacement represent spectral power in the red region of light, and do not necessarily refer to weight percent or molar percent. The broad-band red-emitting phosphor may be partially replaced by the narrow-band red-emitting phosphor in that a determined spectral quantity of spectral output of broad-band red emitting nitride phosphor is replaced by the narrow-band red-emitting phosphor. For example, replacing 50% of the broad-band red-emitting nitride phosphor with the narrow-band red-emitting phosphor can mean that equal proportions of radiative power from each of the red-emitting phosphors are present in the composite spectrum from light source 102.

Replacing at least some of the broad-band red-emitting phosphor with the narrow-band red-emitting phosphor can provide improved color quality metrics, such as CRI, $R_9$, GAI, and/or LPI. An increase in $LPW_r$ (lumens per radiated watt, which is a measure of spectrum efficiency) may be obtained by replacement of at least some of the broad-band red-emitting phosphor with the narrow-band red-emitting phosphor.

The table below lists some combinations of red-emitting phosphors that may be used to form the phosphor 110 shown in FIG. 1.

| Amount | CRI | $R_9$ | GAI | LPI | LPWr |
|--------|-----|-------|-----|-----|------|
| 0%     | 86  | 31    | 27  | 94  | 275  |
| 25%    | 94  | 61    | 28  | 102 | 289  |
| 50%    | 93  | 83    | 29  | 104 | 301  |
| 100%   | 84  | 85    | 30  | 110 | 321  | where the first column of the above table indicates the percentage of the total radiative power from the red phosphor 110 that is from the narrow-band red-emitting phosphor, the second column of the table indicates the Color Rendering Index (CRI) value for the composite spectrum from light source 102, the third column indicates the $R_9$ value for the fidelity of a standard, saturated red for the composite spectrum from light source 102, the fourth column represents the gamut area index (GAI) for the composite spectrum from light source 102 (which is indicative of the relative separation of object colors illuminated by a light source), the fifth column represents the Lighting Preference Index (LPI) as described in published International Application WO-2015-035425 for the composite spectrum from light source 102, and the sixth column represents the lumens per radiated watt (LPWr) for the composite spectrum from light source 102. The CCT of the light generated by the various combinations of phosphors in the preceding table is about 2000 K (e.g., 2043 K) with a Duv value of 0.000. As shown in the table, significant gains in at least the following metrics were seen as a result of replacing of 100% of the broad red emitter with the narrow-band red emitter: $R_9$ (from 31 to 85), GAI (from 27 to 30), LPI (from 94 to 110), and LPWr (from 275 to 321).

Figure 1B:
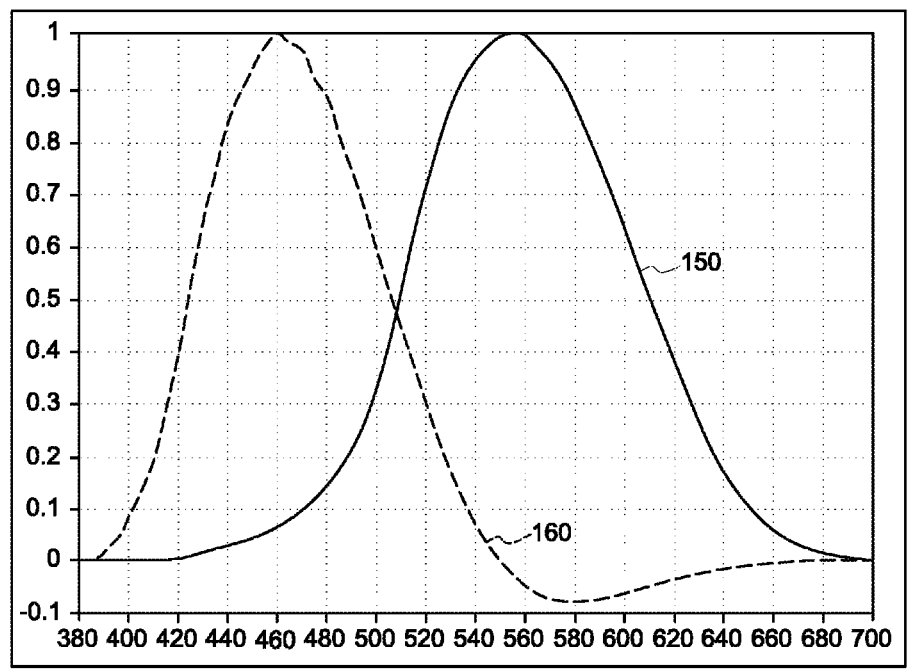
FIG. 1b illustrates the action spectra for photopic and circadian lumens.

FIG. 1b illustrates the action spectra 150 and 160 pertaining to the photopic lumen and circadian lumen ("blue light"), respectively. The photopic lumen flux of a light source is given by the integral over the visible spectrum (from 380 to 760 nm) of the action spectrum 150 for photopic lumens with the SPD of the light source. The circadian lumen flux of a light source is given by the integral over the visible spectrum (from 380 to 760 nm) of the action spectrum 160 for circadian lumens with the SPD of the light source.

Figure 2:
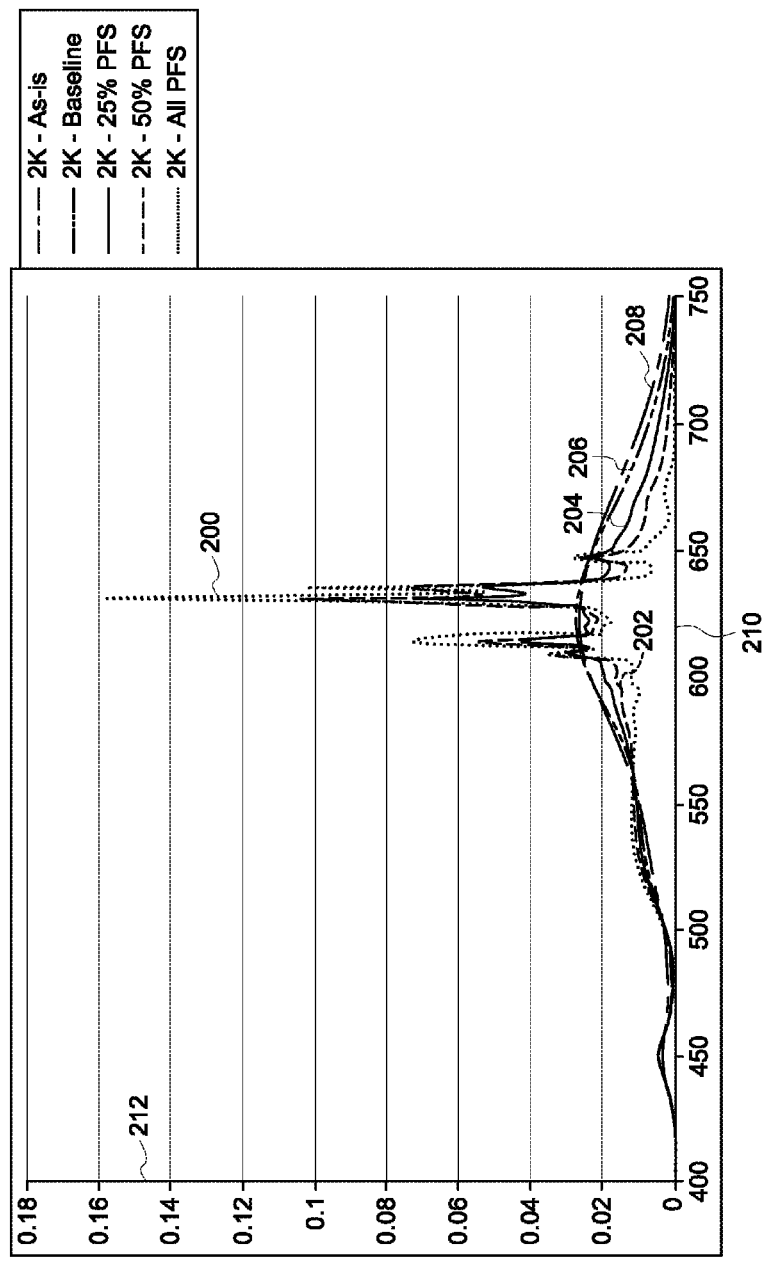
FIG. 2 illustrates spectral power distributions for various embodiments of a low-blue light source shown in FIG. 1a according to one example.

FIG. 2 illustrates SPDs for various embodiments of the light source 102 shown in FIG. 1a according to one example. The spectral power distributions include SPDs 200, 202, 204, 206, 208, which are shown alongside a horizontal axis 210 representative of wavelengths of light generated by the light source 102 and a vertical axis 212 representative of radiant powers emitted by the light source 102 at the different wavelengths. The distribution 200 represents the light source 102 having a phosphor 110 that is formed from 100% of the narrow-band red-emitting phosphor. The distribution 202 represents the light source 102 having a phosphor 110 that results in 50% radiated power by the broad-band red-emitting phosphor and 50% radiated power by the narrow-band red-emitting phosphor. The distribution 204 represents the light source 102 having a phosphor 110 that results in 75% radiated power by the broad-band red-emitting phosphor and 25% radiated power by the narrow-band red-emitting phosphor. The distribution 206 represents the light source 102 having a phosphor 110 that is formed from 100% of the broad-band red-emitting phosphor. The distribution 208 represents the light generated by a known light source, such as the GE ALIGN PM light source.

As shown by the SPDs in FIG. 2, the distributions 200, 202 (and especially the distribution 200) exhibit large increases in spectral power in the light having wavelengths between 600 and 650 nanometers when compared to the other distributions shown in FIG. 2. This can indicate that the significant gains in the power of these wavelengths of light is obtained by replacing 50% or 100% of the broad red emitter with the narrow-band red emitter in the phosphor 110.

With respect to the light source 104, the light source 104 can include one or more blue pumping LEDs 106 having a phosphor 112 disposed thereon. The phosphor 112 may represent coatings or covers on the LED 106 that convert or partially convert the light generated by the LED 106. For example, the phosphor 112 may represent a yellow phosphor coating (e.g., a coating formed from yttrium aluminum garnet, or YAG) that partially converts the blue light generated by the LED 106 to yellow light for mixing with some transmitted blue light. Alternatively, the phosphor 112 may represent combinations of phosphors, such as a blend of a yellow phosphor (e.g., YAG) and a red phosphor (e.g., broad red nitride or narrow red emitter), or multiple types of yellow and/or red phosphors, or other combinations.

The light source 104 can generate light having a CCT of greater than about 3200 K up to about 15,000 K, or even higher. Such a high CCT light with high blue content may have health benefits by suppressing melatonin, which thereby allows a user to more easily regulate his or her sleep cycle or circadian rhythm, particularly in the morning when the user wakes up.

The table below lists different characteristics of different embodiments of the light source 104.

| Type | CRI | $R_9$ | GAI | LPI | LPWr |
|---|---|---|---|---|---|
| Baseline | 72 | −19 | 88 | 84 | 316 |
| Shifted YAG | 80 | 15 | 94 | 91 | 305 |
| Shifted YAG + PFS | 84 | 60 | 99 | 99 | 308 | where the first column of the above table indicates the embodiment of the light source 104 (with different types of phosphors 112 on the LED 106), the second column indicates the CRI value for the corresponding embodiment, the third column indicates the $R_9$ value for the corresponding embodiment, the fourth column represents the GAI for the corresponding embodiment, the fifth column represents the Lighting Preference Index for the corresponding embodiment, and the sixth column represents the lumens per radiated watt for the corresponding embodiment. The CCT of the light generated by the various embodiments in the table is about 7000 K with a Duv value of 0.000.

The "Baseline" embodiment represents a blue pumping LED 106 generating a light with a high color temperature having zero or substantially zero spectral power produced by a red emitter (e.g., broad red nitride or narrow red phosphor). The "Shifted YAG" embodiment of the light source 104 includes the blue pumping LED 106 with a YAG phosphor 112 having a peak wavelength moved or shifted from about 550 nanometers (with a full width at half maximum, or FWHM, of about 110 nanometers) to about 540 nanometers (with a FWHM of about 110 nanometers). The "Shifted YAG" embodiment also includes a red emitter to provide a broad red contribution to the light that is generated, such as a modeled broad-band red-emitting nitride phosphor with a peak emission wavelength of about 620 nanometers and a FWHM width of about 85 nanometers. This red emitter can be included in the phosphor 112 or added as an additional phosphor coating, similar to as described above in connection with the phosphors 108, 110. The red emitter can help maintain the color and CCT of the light at selected or designated values (e.g., 7000 K, or any CCT in the range from about 3200 K to about 15,000 K, or even higher). The embodiment referred to as "Shifted YAG+PFS" refers to a light source 104 which is the same as the "Shifted YAG" embodiment, except that all of the red contribution to the generated light spectrum is derived from a modeled (narrow-red) emitting spectrum, rather than a modeled broad-band red-emitting nitride phosphor (as in the "Shifted YAG" embodiment).

As shown in the preceding table, a high-blue component light source 104 referred to as "Shifted YAG+PFS" had unexpectedly higher CRI, $R_9$, GAI, and LPI values than comparative high-blue component light sources not using a narrow red emitter (or not containing red emitters that are derived from the emission spectrum of PFS phosphor). Using a narrow red emitter instead of nitride resulted in higher spectral efficacy (lumens per radiated watt).

Figure 3:
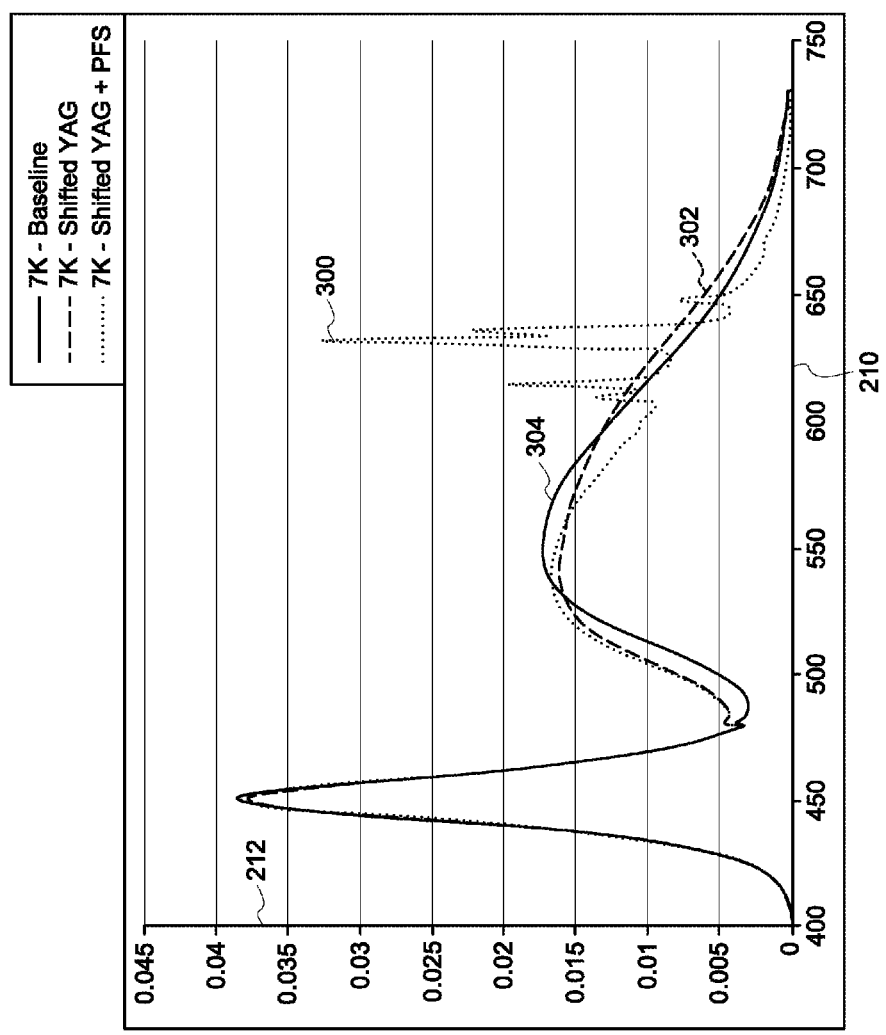
FIG. 3 illustrates spectral power distributions for various embodiments of a high-blue light source shown in FIG. 1a according to one example.

FIG. 3 illustrates SPDs for various embodiments of the light source 104 shown in FIG. 1a according to one example. The spectral power distributions include SPDs 300, 302, 304, which are shown alongside the axes 210, 212 described above. The distribution 304 represents the light generated by the light source 104 having no red phosphor or other red emitter (e.g., only YAG phosphor with peak wavelength at about 550 nm comprising phosphor 112), or the "Baseline" embodiment described above. The distribution 302 represents the light generated by the light source 104 having a YAG phosphor (with peak wavelength at about 540 nm and FWHM of about 110 nm) and broad red nitride phosphor (with peak wavelength at about 620 nm and FWHM of about 85 nm) comprising phosphor 112, or the "Shifted YAG" embodiment. The distribution 300 represents the light generated by the light source 104 having a YAG phosphor 112 of the "Shifted YAG" embodiment, but with all of the red contribution to the generated light spectrum derived from a modeled (narrow-red) emitting spectrum. As is shown in FIG. 3, the "Shifted YAG+PFS" embodiment of the light source 104 provides greater intensities of light having wavelengths about 600 nanometers to about 650 nanometers relative to other embodiments.

The lamp system 100 shown in FIG. 1a may generate light formed from a mixture of the spectra of the two different types of component light sources 102, 104 described above. The mixing of the spectra can be controlled to create an intermediate CCT in the range between the CCTs of the component light sources 102 and 104, for example between about 2500 K and about 3200 K, or preferably to create a warm-white light with a CCT in a range of from about 2700 K to about 3000 K. This type of intermediate or warm-white light is preferred by many consumers. The low-blue, low CCT component light source 102 and the high-blue, high CCT light source 104, in combination, may result in an enhanced, general purpose light that can be used throughout the day. In one or more embodiments, the color point of the light generated by the light system 100 may be below the blackbody locus but near to the white line (or "white body locus") or near to the preference locus, which can result in a more preferred light for many consumers than typical intermediate or warm-white lamps near the blackbody.

The table below illustrates various warm-white embodiments of the light system 100 formed from different combinations of some of the embodiments of the light sources 102, 104 described above.

| High-blue Light Source 104 | Low-Blue Light Source 102 | CRI | R$_9$ | GAI | LPI | LPWr |
|---|---|---|---|---|---|---|
| Baseline | Baseline | 87 | 51 | 79 | 104 | 290 |
| Baseline | 25% PFS | 91 | 75 | 82 | 108 | 300 |
| Baseline | 50% PFS | 93 | 93 | 84 | 114 | 307 |
| Baseline | 100% PFS | 90 | 81 | 87 | 121 | 319 |
| Shifted YAG + PFS | Baseline | 92 | 71 | 81 | 109 | 288 |
| Shifted YAG + PFS | 25% PFS | 93 | 94 | 84 | 115 | 297 |
| Shifted YAG + PFS | 50% PFS | 91 | 87 | 86 | 119 | 304 |
| Shifted YAG + PFS | 100% PFS | 86 | 63 | 89 | 123 | 315 |

The first column in the above table indicates the embodiment of the high-blue light source 104 and the second column indicates the embodiment of the low-blue light source 102 that are included in one embodiment of the system 100. The third through seventh columns indicate the values of CRI, R$_9$, GAI, LPI, and LPWr, as described above, for the corresponding embodiment of the system 100. The color temperature of the light generated by these embodiments of the system 100 is about 3000 K with a Duv of −0.013.

As shown in the preceding table, the embodiments of the system 100 that include light sources 102, 104 with a narrow red emitter in one or more of the components 108, 110, 112 provide light with larger GAI values and LPI values relative to the same lamp system 100 that does not include any narrow red emitters in one or more of the components 108, 110, 112. The inventors of the subject matter described herein have discovered that, as more narrow red emission is included in the components 108, 110, 112 of the light source 102 and/or the light source 104, the values of GAI and LPI increase. Additionally, some embodiments of the system 100 that comprise 25% or 50% narrow red emitters in the low-blue light source 102 had both very high CRI and very high R$_9$. For example, the embodiment of the system 100 having the "Shifted YAG+PFS" light source 104 and the "25% PFS" light source 102 had a CRI of 93 (on a scale which has 100 as a maximum) and R$_9$ of 94. In many of the embodiments shown in the preceding table, replacing the nitride in the phosphor with narrow red emitters also resulted in higher spectral efficacy (LPWr), such as in the embodiments of the system 100 that include the "100% PFS" embodiment of the light source 102.

In one embodiment, the substantially intermediate light that is emitted from the system 100 includes one or more of an R$_9$ value of at least 80, a Gamut Area Index value of at least 80, and/or a Lighting Preference Index value of at least 110.

Figure 4:
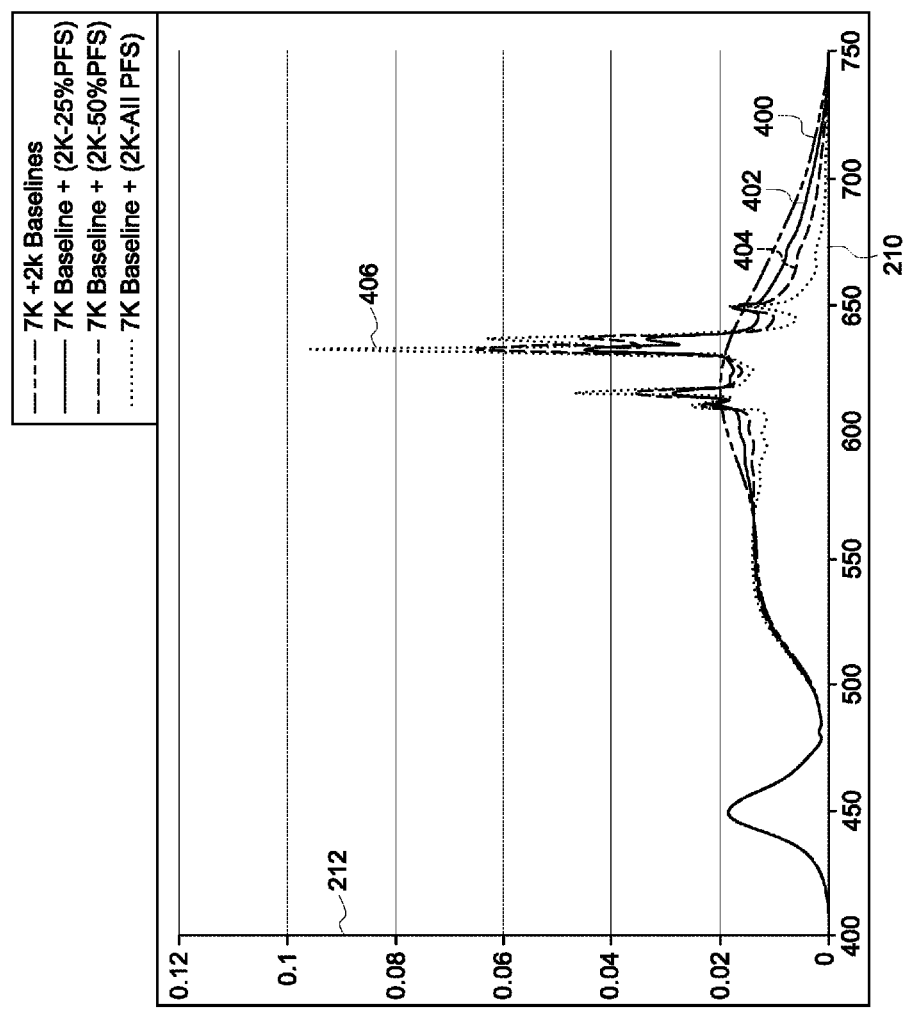
FIG. 4 illustrates spectral power distributions for various embodiments of the lamp system shown in FIG. 1a according to one example.
Figure 5:
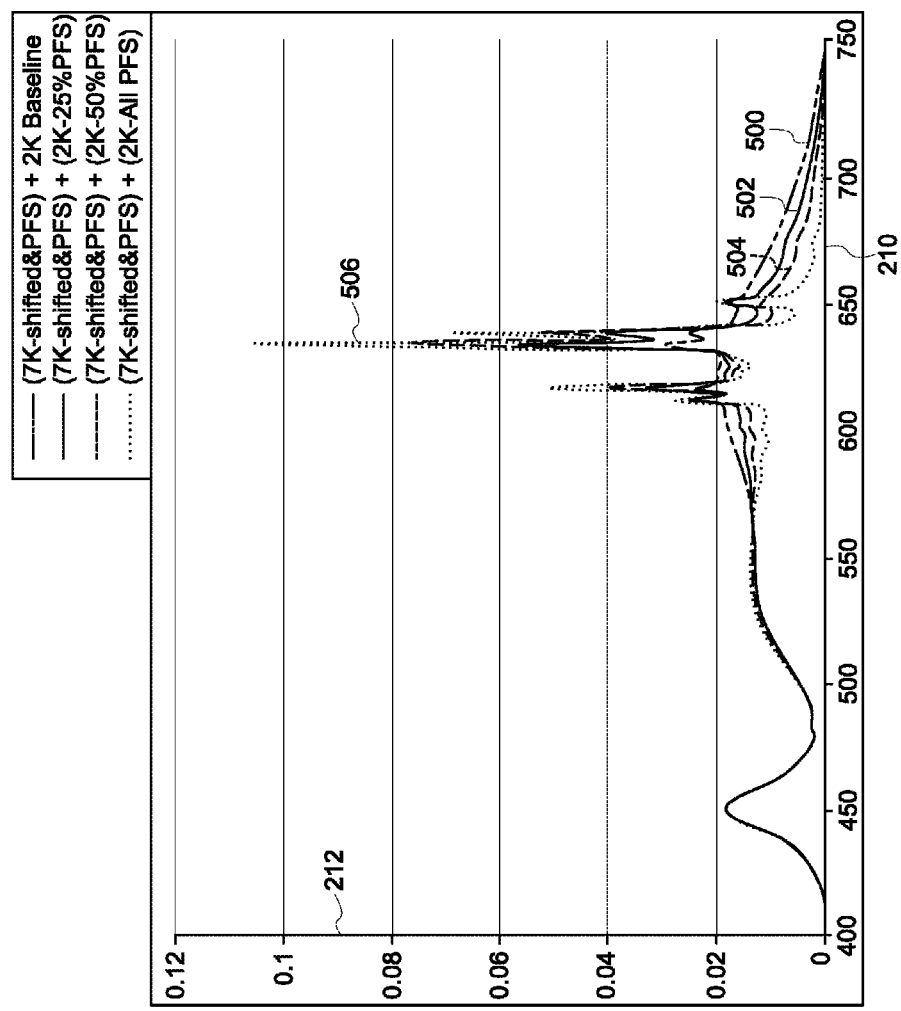
FIG. 5 illustrates spectral power distributions for additional embodiments of the lamp system shown in FIG. 1a according to one example.

FIGS. 4 and 5 illustrate SPDs for various embodiments of the multi-channel lamp system 100 shown in FIG. 1a according to one example. The spectral power distributions shown in FIG. 4 include distributions 400, 402, 404, 406 and the spectral power distributions shown in FIG. 5 include distributions 500, 502, 504, 506. These distributions are all shown alongside the axes 210, 212 described above.

In FIG. 4, the distribution 400 represents the light generated by the system 100 with both the "Baseline" high blue light source 104 and the "Baseline" low-blue light source 102 concurrently generating light. The distribution 404 represents the light generated by the system 100 with both the "Baseline" high-blue light source 104 and the "50% PFS" low-blue light source 102 concurrently generating light. The distribution 406 represents the light generated by the system 100 with both the "Baseline" high-blue light source 104 and the "100% PFS" low-blue light source 102 concurrently generating light.

In FIG. 5, the distribution 500 represents the light generated by the system 100 with both the "Shifted YAG+PFS" high-blue light source 104 and the "Baseline" low-blue light source 102 concurrently generating light. The distribution 502 represents the light generated by the system 100 with both the "Shifted YAG+PFS" high-blue light source 104 and the "25% PFS" low-blue light source 102 concurrently generating light. The distribution 504 represents the light generated by the system 100 with both the "Shifted YAG+PFS" high-blue light source 104 and the "50% PFS" low-blue light source 102 concurrently generating light. The distribution 506 represents the light generated by the system 100 with both the "Shifted YAG+PFS" high-blue light source 104 and the "100% PFS" low-blue light source 102 concurrently generating light.

As shown in FIGS. 4 and 5, a first embodiment of the lamp system 100 having the "Baseline" high-blue light source 104 and the "100% PFS" low-blue light source 102 and a second embodiment of the lamp system 100 having the "Shifted YAG+PFS" high-blue light source 104 and the "100% PFS" low-blue light source 102 produce light spectra having unexpectedly large intensities of light having wavelengths from about 600 nanometers to about 650 nanometers compared to the other embodiments of the lamp system 100. The second embodiment of the lamp system 100 having the "Shifted YAG+PFS" high-blue light source 104 and the "100% PFS" low-blue light source 102 produces a light spectrum having larger intensities from about 600 nanometers to about 650 nanometers compared to the first embodiment of the lamp system 100.

Figure 6:
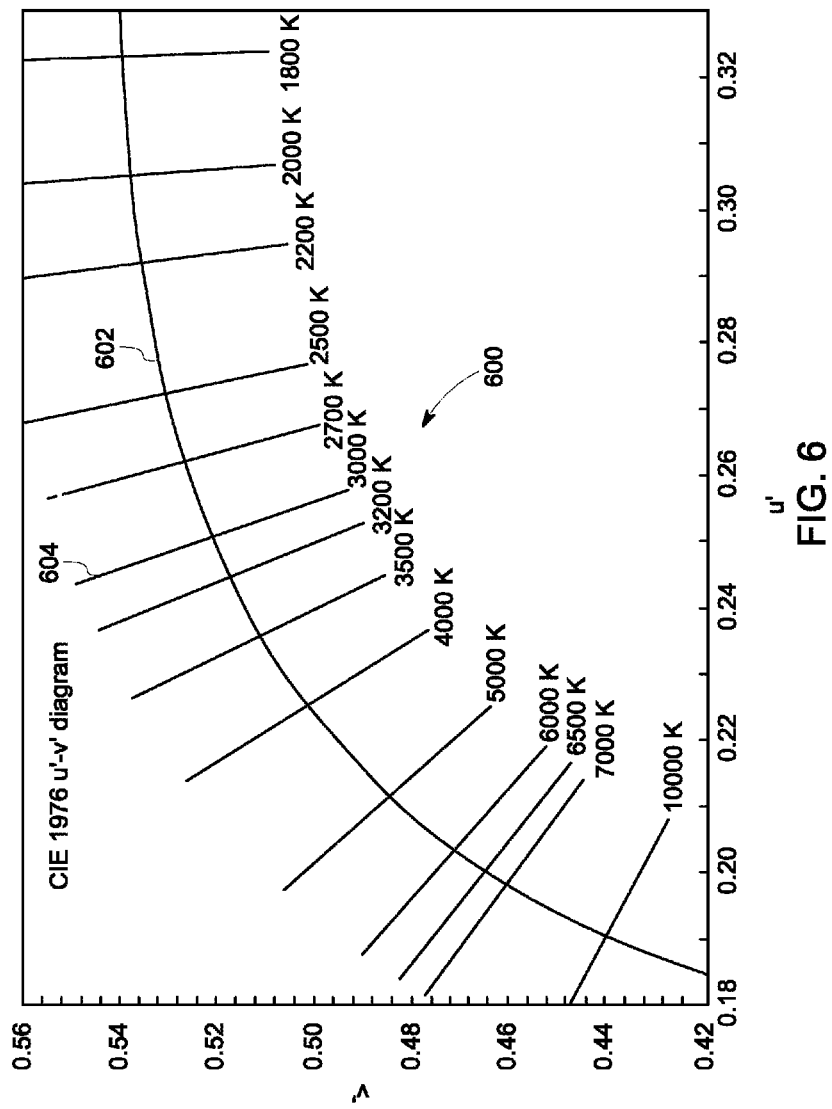
FIG. 6 illustrates a blackbody (Planckian) locus or line ("BBL") in u', v' chromaticity space.

FIG. 6 illustrates a blackbody (Planckian) locus or line ("BBL") 602 in u', v' chromaticity space 600 (e.g., the International Commission on Illumination, or CIE, 1976 u', v' chromaticity space). The chromaticity space 600 may be referred to as color space. Several iso-temperature contours 604 are shown in FIG. 6, with the contours 604 ranging from a CCT of less than 1800 K to a CCT greater than 10,000 K. The illustrated isothermal contour 604 represents a CCT of 3000 K. Isothermal contours are generally perpendicular to the BBL, extending above and below the BBL. The distance away from the BBL is calculated as Duv, or a Euclidean distance in CIE 1960 uv chromaticity space, where a positive value corresponds to a distance above the BBL and a negative value corresponds to a distance below the BBL, along the isothermal contour at the given CCT.

Figure 7:
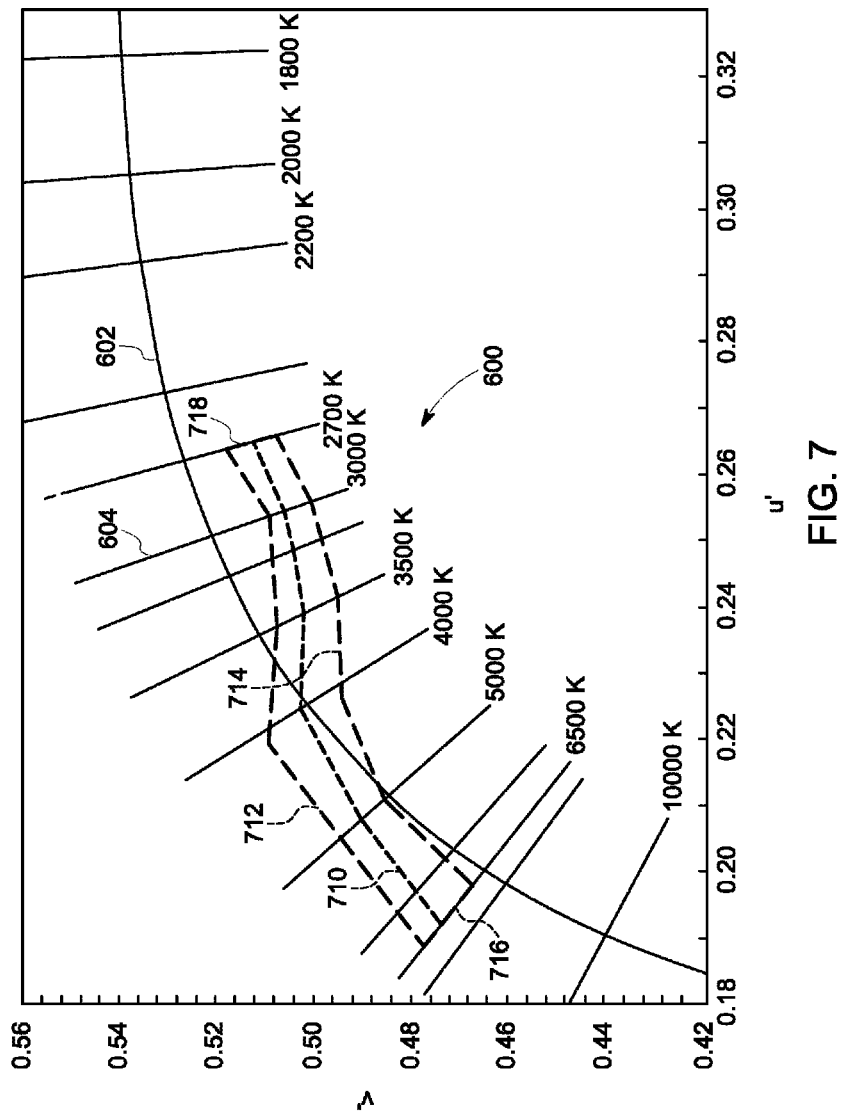
FIG. 7 illustrates a white body locus ("WBL") in the chromaticity space shown in FIG. 6 according to one example.

FIG. 7 illustrates a white body locus ("WBL") 710 in the chromaticity space 600 according to one example. An upper tint limit or boundary 712 and a lower tint limit or boundary 714 of the WBL 710 also are shown in FIG. 7, and the limits represent +/−2% tint. The WBL 710 and tint limits 712, 714 extend from a lower CCT limit or boundary 718 of 2700 K to an upper CCT limit or boundary 716 at 6500 K. The WBL 710 shown in FIG. 7 represents the white body locus described by the 2013 Freysinnier reference. This WBL 710 and the tint limits 712, 714 represent a designated set of CCTs and tints (with different tints representing different distances, or Duv values, along the same isothermal contour 604) that the 2013 Freysinnier reference found to generate a white light that is perceived as having the minimum tint at a given CCT by human subjects. Light having CCTs and tints that are located within the area encompassed by the tint limits 712, 714 and the boundaries 716, 718 provides a white light preferred by human beings.

Figure 8:
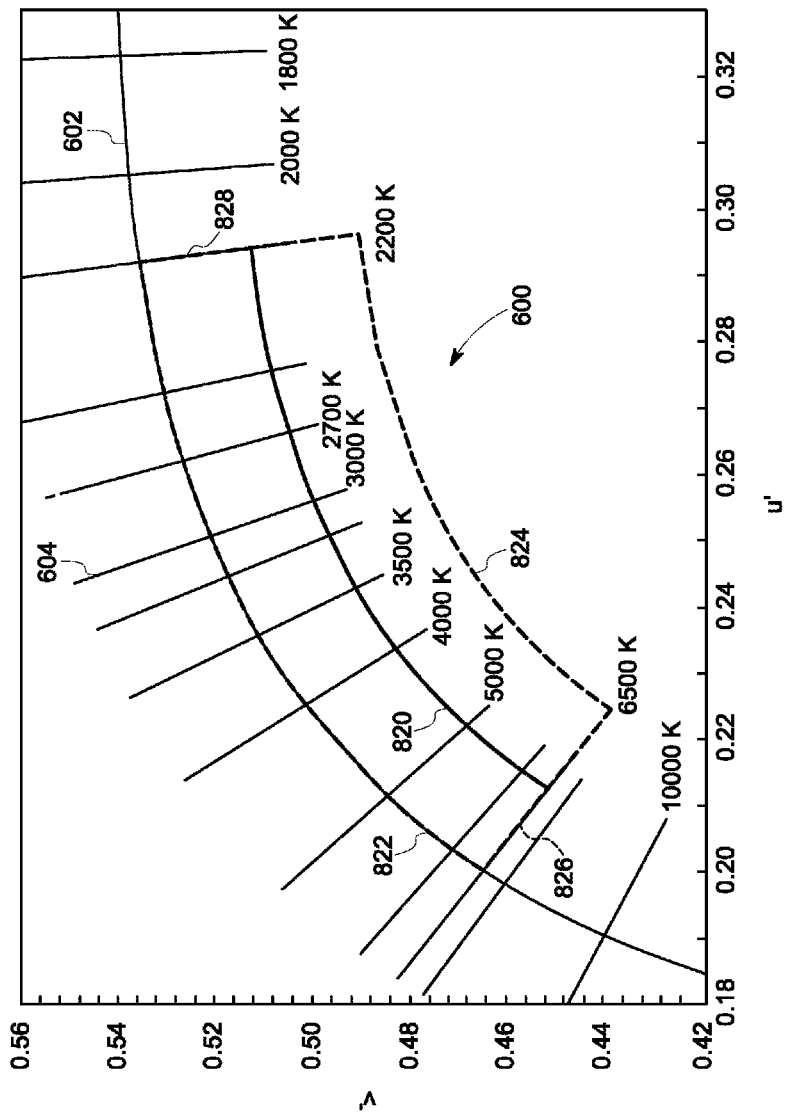
FIG. 8 illustrates a preference locus in the chromaticity space shown in FIG. 6 according to one example.

FIG. 8 illustrates a preference locus 820 in the chromaticity space 600 according to one example. The preference locus 820 is a line that follows the shape of the BBL 602 in chromaticity space 600, but that has a tint that offsets the preference locus 820 from the BBL 602. In the illustrated example, the tint offset is a Duv of −0.015. The preference locus 820 is associated with an upper tint limit or boundary 822 that is coincident with the BBL 602 (e.g., the upper limit 822 has a tint or Duv of zero) and a lower tint limit or boundary 824 that has a tint offset of Duv of −0.030 from the BBL 602. The preference locus 820 and limits 822, 824 are generally determined from the 2015 Ohno reference as providing CCTs and tints that yield white lights that appear more natural to human subjects. The preference locus 820 and limits 822, 824 extend from a lower CCT boundary or limit 828 at 2200 K to an upper CCT limit or boundary 826 at 6500 K. Light having CCTs and tints that are located within the area encompassed by the limits 822, 824 and the boundaries or limits 826, 828 provides a warm-white light preferred by human beings.

Figure 9:
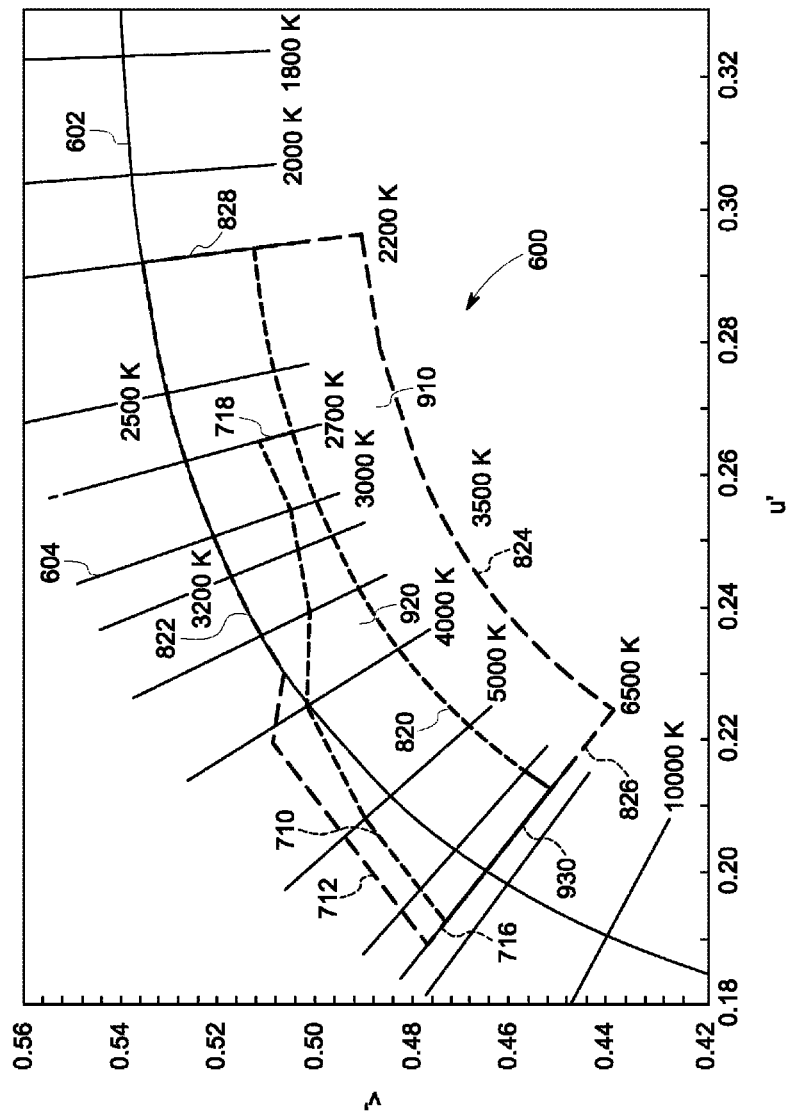
FIG. 9 illustrates a designated area of preferred colors in the chromaticity space shown in FIG. 6 according to one embodiment.

FIG. 9 illustrates a designated area of preferred color points in the chromaticity space 600 according to one embodiment. The designated area is formed as a union or combination of the WBL 710 and associated tint limits 712, 714 shown in FIG. 7, along with the preference locus 820 and limits 822, 824 shown in FIG. 8. The designated area includes an outer area 910 bounded by the lower limit 824 shown in FIG. 8, the upper CCT limits 716, 826, the lower CCT limit 828, and a combination of the upper limits 712, 822 shown in FIGS. 7 and 8. The upper CCT limits 716, 826 coincide to form a combined upper CCT limit or boundary 930 of the outer designated area. An internal or inner area 920 represents more preferred colors, and is bounded by the WBL 710, the lower CCT limit 718, the preference locus 820, and the combined upper CCT limit 930. Colors falling within the inner designated 920 area may represent white light that is more preferred by human subjects than colors falling within the outer designated area 910, but colors falling within the outer designated area 910 may be more preferred as white light than colors falling outside of the outer designated area 910. Herein, the term "color(s)" is used interchangeably with "chromaticity(ies)"; not to infer a saturated hue, but rather any locus in the chromaticity space.

In accordance with one or more embodiments described herein, the light sources 102, 104 shown in FIG. 1a may be selected so that a tie line that connects the color points of the sources 102, 104 in chromaticity space 600 extends across, over, or through one or more designated areas within the outer and/or inner designated areas of preferred colors set forth in FIG. 9. A combination of light sources 102, 104 that are connected by a tie line extending across, over, or through one or more designated areas within the outer and/or inner designated areas of preferred colors can provide a white light that is preferred by human subjects over other white lights, which may be too pink, too yellow, too green, etc., for human preferences.

Figure 10:
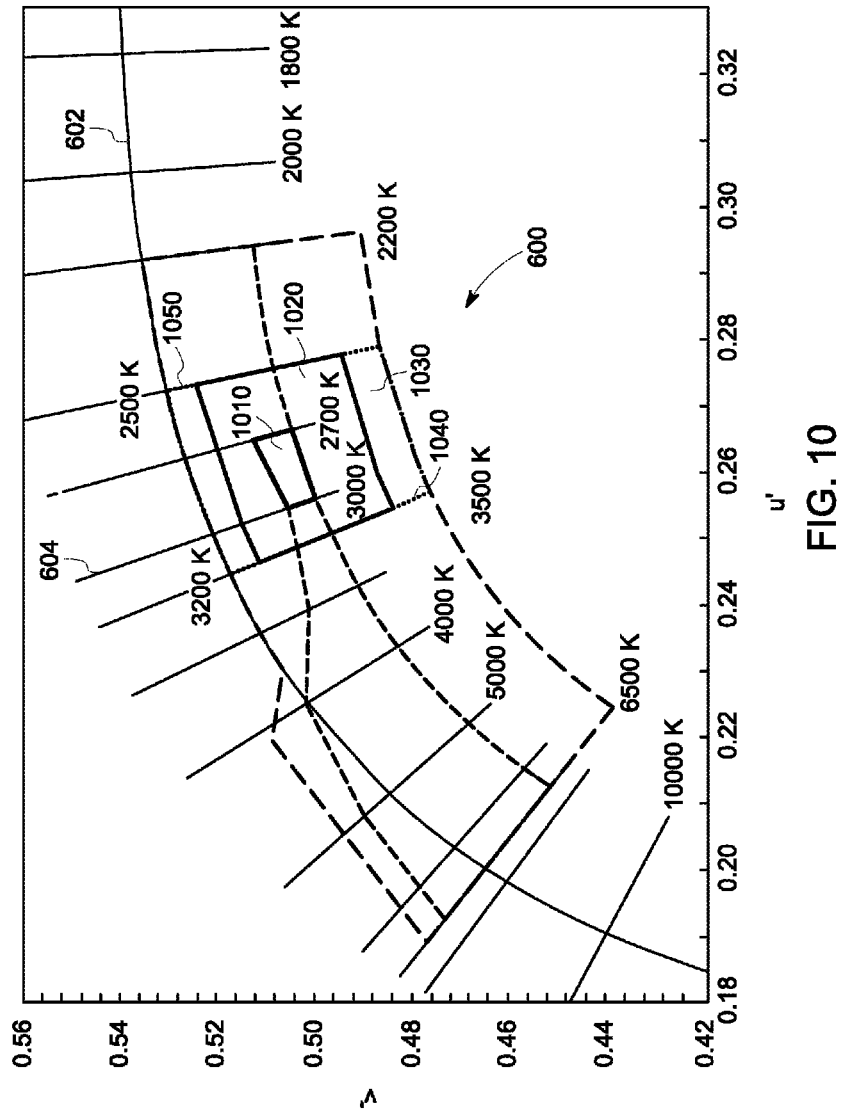
FIG. 10 illustrates designated preferred zones in the chromaticity space shown in FIG. 6 according to one embodiment.

FIG. 10 illustrates three designated preferred zones 1010, 1020, 1030 in the chromaticity space 600 according to one embodiment. The zone 1010 is bounded by the lower CCT limit 718 (at 2700 K) of the WBL 710 shown in FIG. 7, the preference locus 820 shown in FIG. 8, a designated isothermal contour 604 at 3000 K, and the WBL 710 shown in FIG. 7. Alternatively, one or more other boundaries may be selected for the zone 1010. For example, since the upper and lower boundaries of the zone 1010 are determined by color preference research that provides approximate curves for observer perceptions of whiteness and of naturalness, it may be expected that the zone 1010 might be slightly higher or lower in the Duv direction, but not as high or low as the upper and lower limits of zone 1020. The zone 1010 can represent the colors that are most preferred for warm-white light in the range 2700 K to 3000 K over one or more other sets or areas in chromaticity space 600.

The zone 1020 represents colors that are preferred for warm-white light in the range 2500 K to 3200 K over one or more other sets or areas in chromaticity space 600 other than the zone 1010. For example, the colors encompassed by the zone 1010 may be preferred over the colors encompassed by the zone 1020 for producing a warm-white light, but the colors encompassed by the zone 1020 may be preferred for a warm-white light over colors outside of the zone 1020. The zone 1020 is bounded by a designated isothermal contour 604 at 2500 K for a lower CCT boundary 1040, a lower tint limit or boundary that follows the contour of the preference locus 820 but that is offset from the preference locus 820 by a Duv of −0.010 or offset from the BBL 602 by a Duv of −0.025, a designated isothermal contour 604 at 3200 K for an upper CCT boundary 1050, and an upper tint limit or boundary that follows the contour of the preference locus 820 but that is offset from the preference locus 820 by a Duv of +0.010 or offset from the BBL 602 by a Duv of −0.005. Alternatively, one or more of the boundaries 1040, 1050 of the zone 1020 may extend along different CCTs and/or be offset from the preference locus 820 by a different amount. For example, since the upper and lower boundaries of the zone 1020 are determined by color preference research that provides approximate curves for observer perceptions of whiteness and of naturalness, it may be expected that the zone 1020 might be slightly higher or lower in the Duv direction, but not as high or low as the upper and lower limits of zone 1030.

The zone 1030 represents colors that are preferred for warm-white light in the range 2500 K to 3200 K over one or more other sets or areas in chromaticity space 600 other than the zones 1010, 1020. For example, the colors encompassed by the zones 1010, 1020 may be preferred over the colors encompassed by the zone 1030 for producing a warm-white light, but the colors encompassed by the zone 1030 may be preferred for a warm-white light over colors outside of the zone 1030. The zone 1030 is bounded by the lower CCT limit 1050 at 2500 K, the lower tint limit 824, a designated isothermal contour 1040 at 3200 K, and the upper tint limit 822, or BBL 602. Alternatively, one or more of these limits or contours may extend along different CCTs and/or be offset from the preference locus 820 by different amounts.

A variety of different combinations of lights generated by the light sources 102, 104 may be used to generate a warm-white light that falls within one or more of the zones 1010, 1020, 1030. The examples described herein provide some, but not all, combinations of the color points of the lights that may be generated by the light sources 102, 104 to produce a warm white light at a preferred color point. A color point in the chromaticity space 600 represents a color of a light generated by the light source 102 or 104, as described herein. A tie line in the chromaticity space 600 represents a connection between the color points of the light sources 102, 104 in a designated combination of the light sources 102, 104. Several examples provided herein set forth different areas in chromaticity space where color points of the different lights generated by the light sources 102, 104 can be located in order for the light sources 102, 104 to separately provide the low- and high-CCT lights, respectively that are each located at preferred color points, but also so that these light sources 102, 104 can provide a combined light that has a warm-white light falling within one or more of the preferred zones 1010, 1020, 1030 (or another zone). The examples provided herein are not limiting on all embodiments of the inventive subject matter, but provide some techniques for determining the color points (e.g., CCTs, Duv values, etc.) of the lights generated by the light sources 102, 104.

Figure 11:
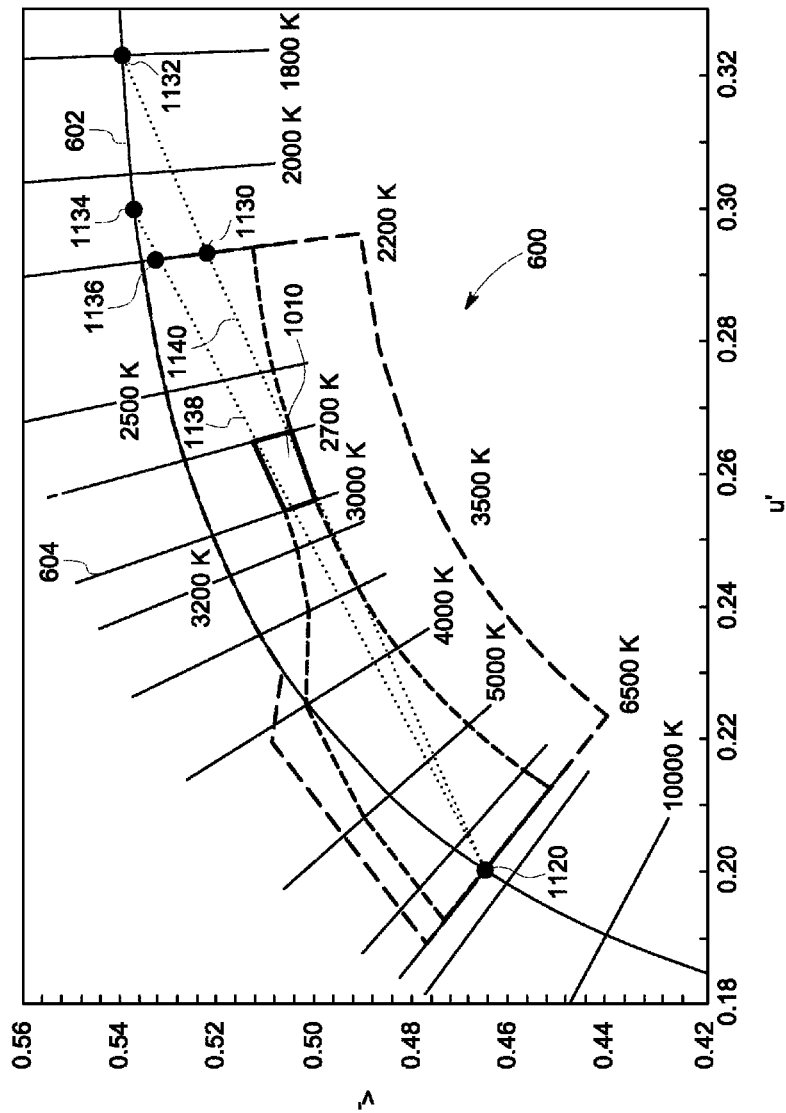
FIG. 11 illustrates examples of combinations of chromaticities of light sources shown in FIG. 1a that may be used to generate a warm-white light within a first preferred zone shown in FIG. 10 according to one embodiment.

FIG. 11 illustrates examples of combinations of light sources 102, 104 that are each located at preferred color points that may be used to generate a warm-white light within the zone 1010 shown in FIG. 10 according to one embodiment. A high-CCT color point 1120 represents the color point or color of light produced by the light source 104. The high-CCT color point 1120 is located at the intersection between the BBL 602 and the limit 930 (shown in FIG. 9 or, the limits 716, 826), and therefore lies at a preferred color point for a high-blue light source having CCT at 6500 K. In order for a light source 102 to be used with the light source 104 to cause a combination of the light sources 102, 104 to produce a warm-white light having a color that is within the zone 1010, a tie line between the color points of the light sources 102, 104 may need to extend across or through the zone 1010. With the color point 1120 of the light source 104, two outer tie lines 1138, 1140 represent the tie lines that extend from or intersect the color point 1120, while also extend over outer edges of the zone 1010, as shown in FIG. 10.

The intersection of the outer tie lines 1138, 1140 with one or more isothermal contours 604 can indicate additional color points 1130, 1132, 1134, 1136 that can represent the color of the light generated by the light source 102, each lying at a preferred color point for a low-blue light source. A combination of a color represented by one or more of these preferred color points 1130, 1132, 1134, 1136 being produced by the light source 102 with the color represented by the preferred color point 1120 of the light source 104 can produce a light having a preferred warm-white light within the zone 1010. The color point 1130 represents a lower tint or Duv limit on the isothermal contour 604 for a CCT of 2200 K and the color point 1136 represents an upper tint or Duv limit on the isothermal contour 604 for the CCT of 2200 K. This indicates that, in order to use a light source 104 producing light with the color point 1120, the light source 102, if located at a CCT of about 2200 K, may need to generate light having a tint or Duv between the limits indicated by the color points 1130, 1136. Alternatively, if a different CCT is to be used for the light source 102, then the range of tints or Duv may be more or less limited. For example, in one embodiment, the color points for the light generated by the light sources 102, 104 remain at or below the BBL 602 in the color space 600. The tie line 1138 extends to a color point 1134 located on the BBL 602, which has a CCT of about 2100 K and a Duv of zero. The tie line 1140 extends to a color point 1132 located on the BBL 602, which has a CCT of about 1800 K and a Duv of zero.

These color points 1130, 1132, 1134, 1136 can represent the outer limits on a range of CCTs and a range of tints (e.g., Duv values) for colors of lights generated by the light source 102 when used in combination with the color point 1120 generated by the light source 104. The color points 1130, 1132, 1134, 1136 can be determined based on the tie lines 1138, 1140 being the tie lines that extend from the color point 1120 and extend across the zone 1010 on the outermost edges of the zone 1010 while also intersecting the BBL 602 and the lower CCT boundary 828 at the color points 1130, 1132, 1134, 1136.

The ranges of CCTs and Duv values can be defined in the color space 600 by a line extending from the color point 1136 to the color point 1134, a line extending along the BBL 602 from the color point 1134 to the color point 1132, a line extending from the color point 1132 to the color point 1130, and a line extending along the lower CCT limit 828 (e.g., along the isothermal contour 604 for 2200 K). A variety of color points falling within the range defined by these lines and/or color points 1130, 1132, 1134, 1336 may be used with the color point 1120 to provide a mixed intermediate light falling within the zone 1010. For example, the four low-CCT color points 1130, 1132, 1134, 1136 define a quadrilateral defining the most preferred zone of color points for a low-CCT light source 102 which, when combined with a high-CCT light source 104 at about 6500 K on or near the BBL 602 provides a combination warm-white light that is most preferred (e.g., that falls or extends across the zone 1010).

Figure 12:
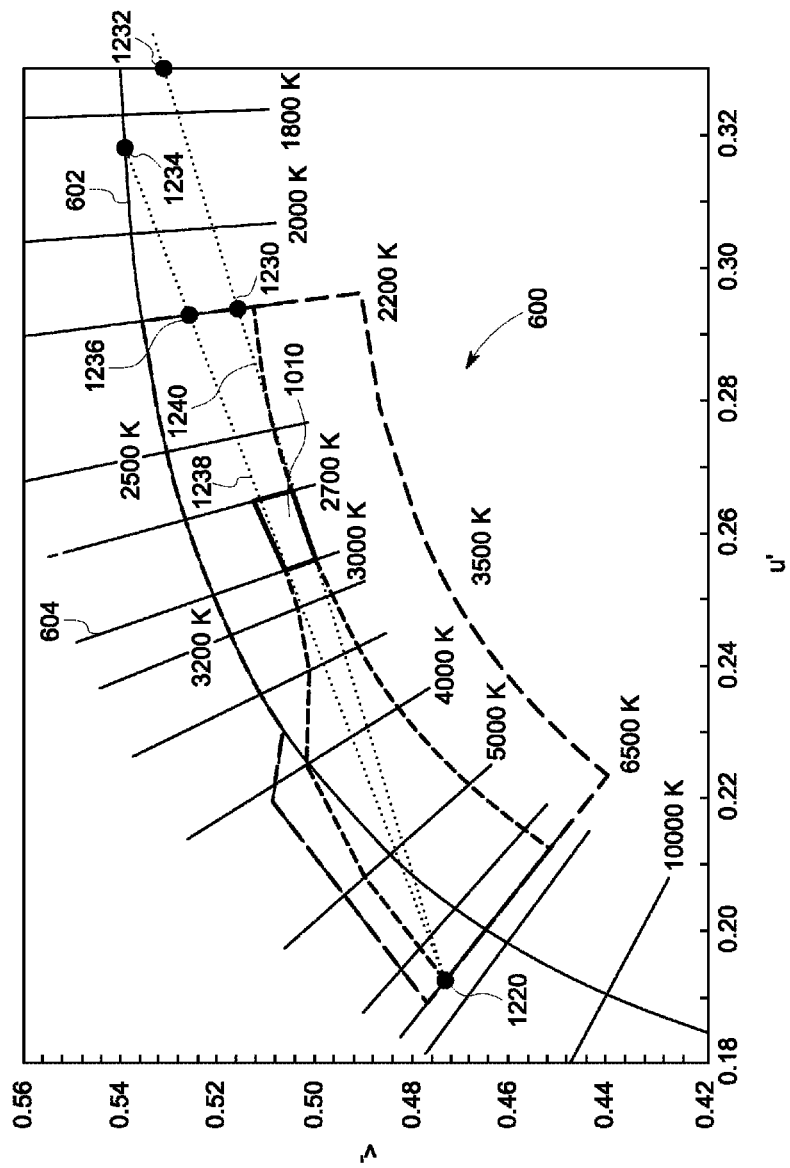
FIG. 12 illustrates additional examples of combinations of chromaticities of light sources shown in FIG. 1a that may be used to generate a warm-white light within the first preferred zone shown in FIG. 10 according to one embodiment.

FIG. 12 illustrates additional examples of combinations of light sources 102, 104 that may be used to generate a warm-white light within the zone 1010 shown in FIG. 10 according to one embodiment. The examples shown in FIG. 12 represent the limits on the color points that may be used for the low-CCT light source 102 when the high-CCT light source 104 has a color point 1220 that is at the intersection of the WBL 710 and the isothermal contour 604 at a CCT of 6500 K (e.g., the boundary 716, 826, 930) and a tie line connecting the color points representing the lights generated by the light sources 102, 104 extends across or through the zone 1010. For example, tie lines 1238, 1240 extend across or along the outer edges or boundaries of the zone 1010. The tie line 1238 intersects the lower CCT boundary 828 at a color point 1236 and the tie line 1240 intersects the lower CCT boundary 828 at a color point 1230. These color points 1230, 1236 can represent limits on the color points extending along the isothermal contour 604 at a CCT of 2200 K that can be used for the low-CCT light source 102. The tie line 1238 intersects the BBL 602 at a color point 1234 and the tie line 1240 intersects the BBL 602 in a location that is not visible in FIG. 12, but that is represented by the color point 1232 and occurs at a CCT of less than 1800 K (e.g., between 1700 and 1000 K).

These color points 1230, 1232, 1234, 1236 can represent the outer limits on a range of CCTs and a range of tints (e.g., Duv values) for colors of lights generated by the light source 102 when used in combination with the color point 1220 generated by the light source 104. The color points 1230, 1232, 1234, 1236 can be determined based on the tie lines 1238, 1240 being the tie lines that extend from the color point 1220 and extend across the zone 1010 on the outermost edges of the zone 1010 while also intersecting the BBL 602 and the lower CCT boundary 828 at the color points 1230, 1232, 1234, 1236. The ranges of CCTs and Duv values can be defined in the color space 600 by a line extending from the color point 1236 to the color point 1234, a line extending from the color point 1234 to the color point 1232, a line extending from the color point 1232 to the color point 1230, and a line extending along the lower CCT limit 828 (e.g., along the isothermal contour 604 for 2200 K). A variety of color points falling within a shape defined by the color points 1230, 1232, 1234, 1236 may be used with the color point 1220 to provide a mixed intermediate light falling within the zone 1010.

Figure 13:
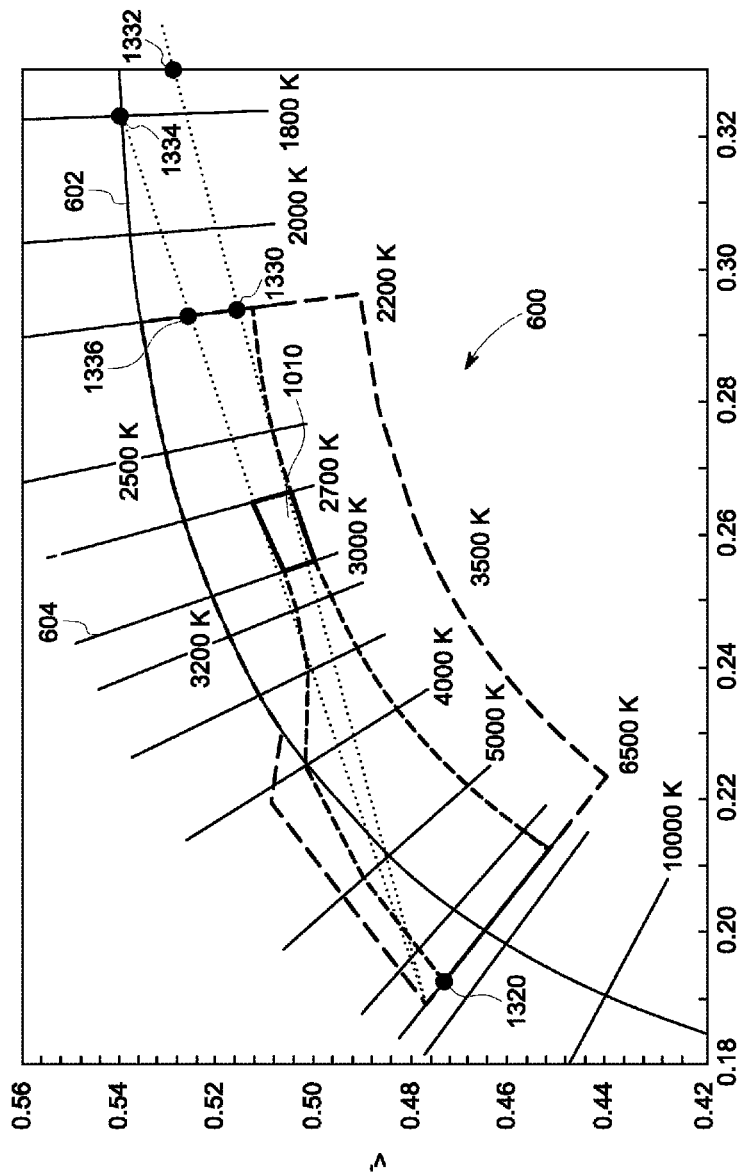
FIG. 13 illustrates additional examples of chromaticities of combinations of light sources shown in FIG. 1a that may be used to generate a warm-white light within the first preferred zone shown in FIG. 10 according to one embodiment.

FIG. 13 illustrates additional examples of combinations of light sources 102, 104 that may be used to generate a warm-white light within the zone 1010 shown in FIG. 10 according to one embodiment. The examples shown in FIG. 13 represent the limits on the color points that may be used for the low-CCT light source 102 when the high-CCT light source 104 has a color point 1320 that is at the intersection of the upper tint limit 712, as shown in FIG. 7, and the isothermal contour 604 at a CCT of 6500 K (e.g., the boundary 716, 826, 930) and a tie line connecting the color points representing the lights generated by the light sources 102, 104 extends across or through the zone 1010.

For example, tie lines 1338, 1340 extend across or along the outer edges or boundaries of the zone 1010. The tie line 1338 intersects the lower CCT boundary 828 at a color point 1336 and the tie line 1340 intersects the lower CCT boundary 828 at a color point 1330. These color points 1330, 1336 can represent limits on the color points extending along the isothermal contour 604 at a CCT of 2200 K that can be used for the low-CCT light source 102. The tie line 1338 intersects the BBL 602 at a color point 1334 and the tie line 1340 intersects the BBL 602 in a location that is not visible in FIG. 13, but that is represented by the color point 1332 and occurs at a CCT of less than 1800 K (e.g., between 1000 and 1700 K).

These color points 1330, 1332, 1334, 1336 can represent the outer limits on a range of CCTs and a range of tints (e.g., Duv values) for colors of lights generated by the light source 102 when used in combination with the color point 1320 generated by the light source 104 (e.g., to cause a combination of light from the sources 102, 104 to fall within the zone 1010). The color points 1330, 1332, 1334, 1336 can be determined based on the tie lines 1338, 1340 being the tie lines that extend from the color point 1320 and extend across the zone 1010 on the outermost edges of the zone 1010 while also intersecting the BBL 602 and the lower CCT boundary 828 at the color points 1330, 1332, 1334, 1336.

The ranges of CCTs and Duv values can be defined in the color space 600 by a line extending from the color point 1336 to the color point 1334, a line extending from the color point 1334 to the color point 1332, a line extending from the color point 1332 to the color point 1330, and a line extending along the lower CCT limit 828 (e.g., along the isothermal contour 604 for 2200 K). A variety of color points falling within the shape defined by the color points 1330, 1332, 1334, 1336 may be used with the color point 1320 to provide a mixed intermediate light falling within the zone 1010.

Figure 14:
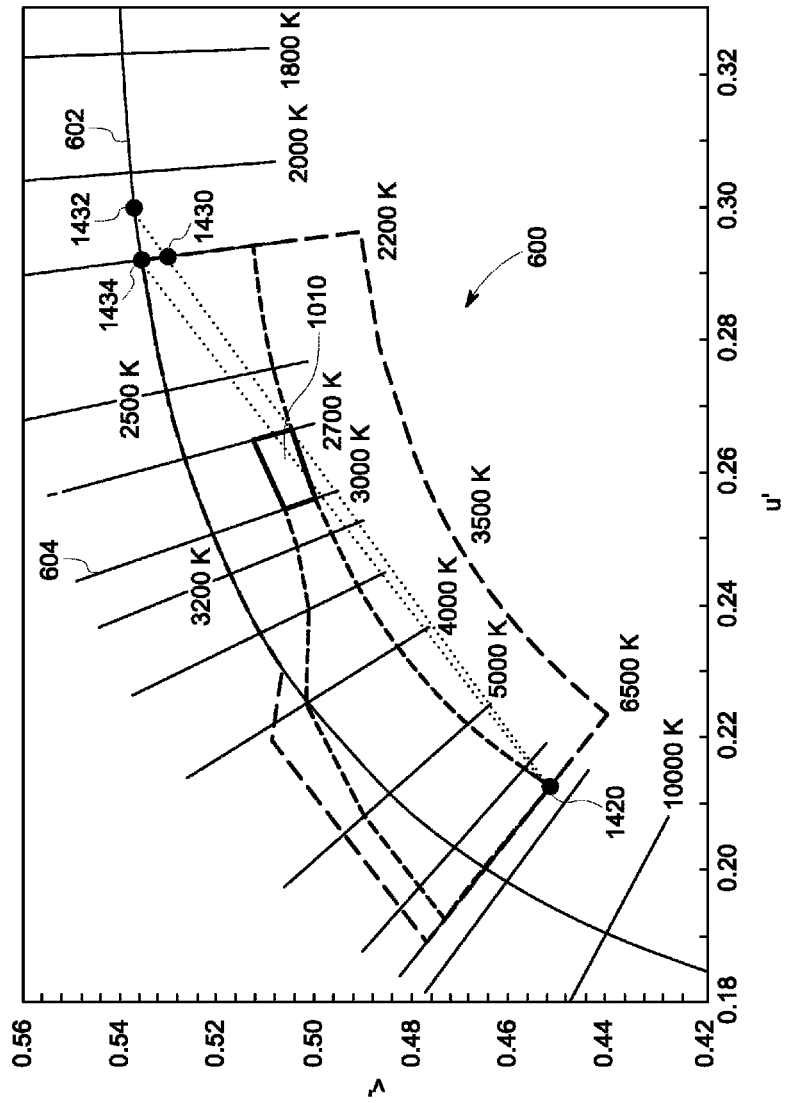
FIG. 14 illustrates additional examples of chromaticities of combinations of light sources shown in FIG. 1a that may be used to generate a warm-white light within the first preferred zone shown in FIG. 10 according to one embodiment.

FIG. 14 illustrates additional examples of combinations of light sources 102, 104 that may be used to generate a warm-white light within the zone 1010 shown in FIG. 10 according to one embodiment. The examples shown in FIG. 14 represent the limits on the color points that may be used for the low-CCT light source 102 when the high-CCT light source 104 has a color point 1420 that is at the intersection of the preference locus 820 and the upper limit 826 (and/or 930) and a tie line connecting the color points representing the lights generated by the light sources 102, 104 extends across or through the zone 1010.

For example, tie lines 1436, 1438 extend across or along the outer edges or boundaries of the zone 1010. The tie line 1436 intersects the BBL 602 and the lower CCT boundary 828 at a color point 1434 and the tie line 1438 intersects the lower CCT boundary 828 at a color point 1430. These color points 1430, 1434 can represent limits on the color points extending along the isothermal contour 604 at a CCT of 2200 K that can be used for the low-CCT light source 102. The tie line 1438 intersects the BBL 602 at a color point 1432.

These color points 1430, 1432, 1434 can represent the outer limits on a range of CCTs and a range of tints (e.g., Duv values) for colors of lights generated by the light source 102 when used in combination with the color point 1420 generated by the light source 104 (e.g., to cause a combination of light from the sources 102, 104 to fall within the zone 1010). The color points 1430, 1432, 1434 can be determined based on the tie lines 1436, 1438 being the tie lines that extend from the color point 1420 and extend across the zone 1010 while also intersecting the BBL 602 and the lower CCT boundary 828.

The ranges of CCTs and Duv values can be defined in the color space 600 by a line extending along the BBL 602 from the color point 1434 to the color point 1432, a line extending from the color point 1432 to the color point 1430, and a line extending along the lower CCT limit 828 (e.g., along the isothermal contour 604 for 2200 K). In contrast to the ranges of CCTs and Duv values in FIGS. 11 through 13 (which form a trapezoid shape or shape approximating a trapezoid), the ranges of CCTs and Duv values in the example of FIG. 14 provide the shape of a triangle, as shown in FIG. 14. A variety of color points falling within the triangular shape defined by the color points 1430, 1432, 1434 may be used with the color point 1420 to provide a mixed intermediate light falling within the zone 1010.

Figure 15:
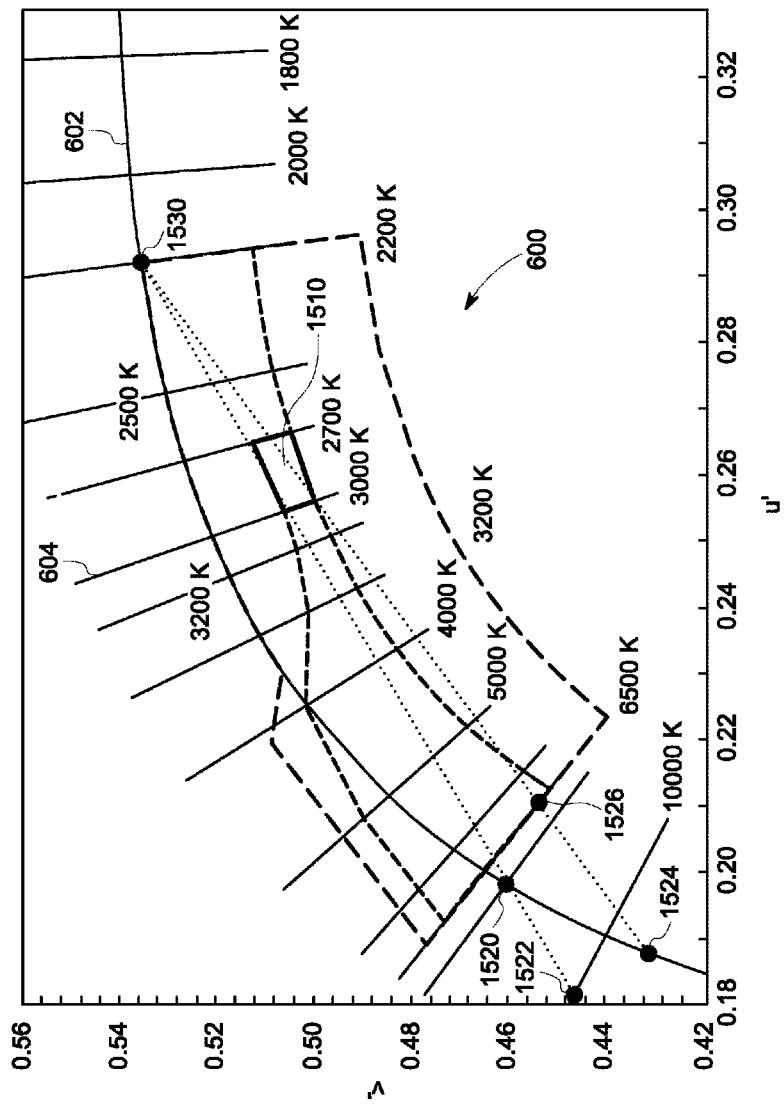
FIG. 15 illustrates additional examples of chromaticities of combinations of light sources shown in FIG. 1a that may be used to generate a warm-white light within the first preferred zone shown in FIG. 10 according to one embodiment.

FIG. 15 illustrates additional examples of combinations of light sources 102, 104 that may be used to generate a warm-white light within the zone 1010 shown in FIG. 10 according to one embodiment. The examples shown in FIG. 15 represent the limits on the color points that may be used for the high-CCT light source 104 when the low-CCT light source 102 has a color point 1530 that is at the intersection of the BBL 602 and the lower CCT limit 828 and a tie line connecting the color points representing the lights generated by the light sources 102, 104 extends across or through the zone 1010.

Tie lines 1528, 1532 extend across or along the outer edges or boundaries of the zone 1010. The tie line 1528 intersects the BBL 602 at a color point 1520 and the tie line 1532 intersects the upper CCT boundary 826, as shown in FIG. 8, at a color point 1526. The tie line 1528 intersects the isothermal contour 604 at 10,000 K at a color point 1522 and the tie line 1532 intersects the BBL 602 at a color point 1524. Alternatively, a CCT other than 10,000 K may be used to determine the color point 1522.

These color points 1520, 1522, 1524, 1526 can represent the outer limits on a range of CCTs and a range of tints (e.g., Duv values) for colors of lights generated by the light source 104 when used in combination with the color point 1530 generated by the light source 102 (e.g., to cause a combination of light from the sources 102, 104 to fall within the zone 1010). The ranges of CCTs and Duv values can be defined in the color space 600 by a line extending from the color point 1520 to the color point 1522, a line extending from the color point 1522 to the color point 1524, a line extending from the color point 1524 to the color point 1526, and a line extending from the color point 1526 to the color point 1520. A variety of color points falling within the shape defined by the color points 1520, 1522, 1524, 1526 may be used with the color point 1530 to provide a mixed intermediate light falling within the zone 1010.

Figure 16:
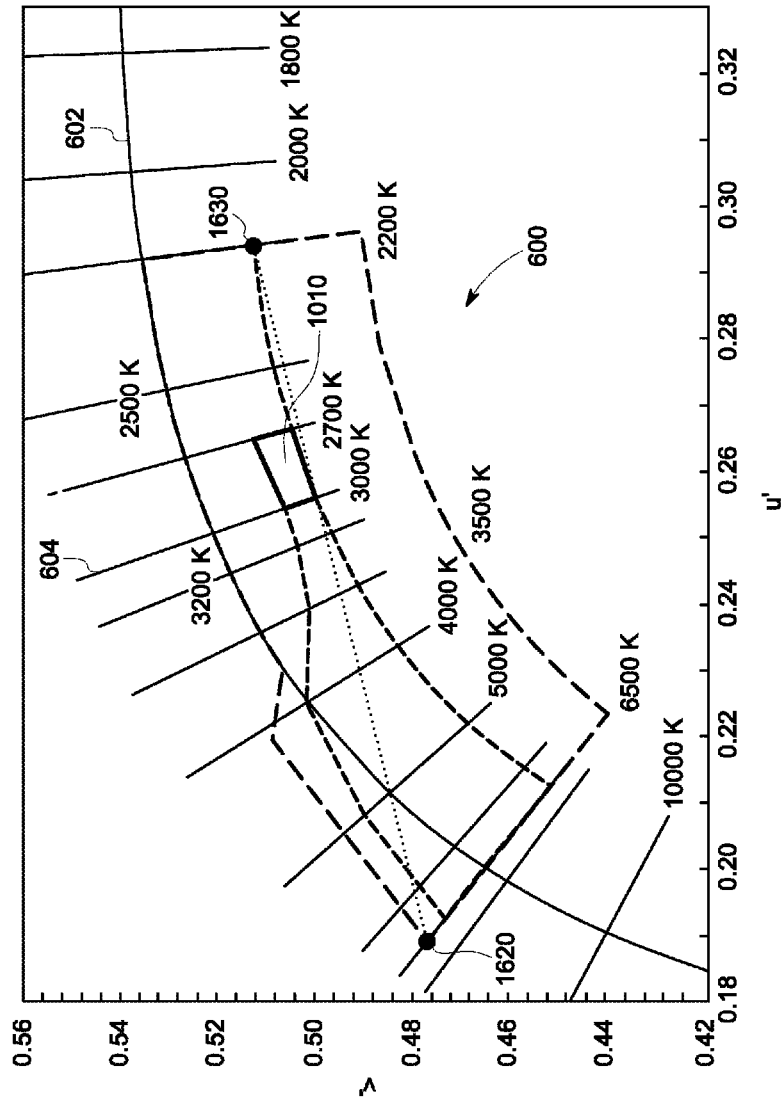
FIG. 16 illustrates an additional example of chromaticities of a combination of light sources shown in FIG. 1a that may be used to generate a warm-white light within the first preferred zone shown in FIG. 10 according to one embodiment.

FIG. 16 illustrates an additional example of a combination of light sources 102, 104 that may be used to generate a warm-white light within the zone 1010 shown in FIG. 10 according to one embodiment. The example shown in FIG. 16 represents the limits on the color points that may be used for the high-CCT light source 104 when the low-CCT light source 102 has a color point 1630 that is at the intersection of the preference locus 820 and the lower CCT limit 828 and a tie line connecting the color points representing the lights generated by the light sources 102, 104 extends across or through the zone 1010. A single tie line 1628 extends across or along the outer edges or boundaries of the zone 1010. The tie line 1628 is oriented such that the tie line 1628 intersects the upper CCT limit 716, as shown in FIG. 7, at the intersection of the upper CCT limit 716 and the upper limit 712 at a color point 1620.

The color point 1620 can represent the CCT and tint (e.g., Duv value) for light generated by the light source 104 when used in combination with the color point 1630 generated by the light source 102 (to cause the combined light to fall within the zone 1010). Because only the tie line 1628 both extends from the color point 1630 and crosses the zone 1010, only a single color point 1620 may be used for the color of the light generated by the light source 104 in the illustrated example.

Since the upper and lower boundaries of the zone 1010 might be expected to be slightly higher or lower in the Duv direction, but not as high or low as the upper and lower limits of zone 1020, it can be generalized that the color point in the warm-white CCT range of 2700 K to 3000 K is most preferred when the high-blue light source 104 at about 6500 K or higher lies within a Duv range of about 0.015 above the BBL to about 0.015 below the BBL, combined with a low-blue light source 102 at about 2200K or lower that lies within a Duv range of about 0.005 above the BBL to about 0.015 below the BBL.

Figure 17:
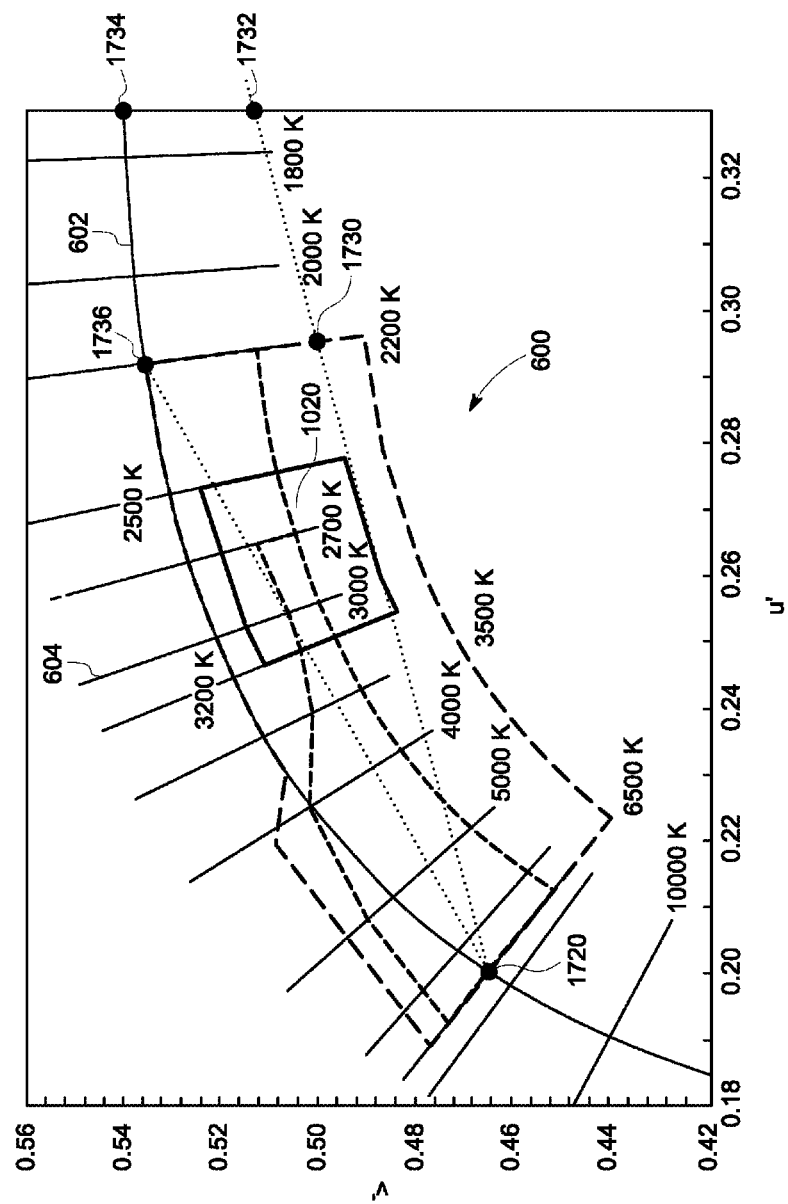
FIG. 17 illustrates examples of chromaticities of combinations of light sources shown in FIG. 1a that may be used to generate a warm-white light within a larger, second preferred zone shown in FIG. 10 according to one embodiment.

FIG. 17 illustrates additional examples of combinations of light sources 102, 104 that may be used to generate a warm-white light within the different zone 1020 shown in FIG. 10 according to one embodiment. While the examples of FIGS. 11 through 16 focus on light from the light sources 102, 104 having tie lines that extend through or across the zone 1010, the example of FIG. 17 describes various color points for the light sources 102, 104 having tie lines that extend across or through the larger zone 1020. The examples shown in FIG. 17 represent the limits on the color points that may be used for the low-CCT light source 102 when the high-CCT light source 104 has a color point 1720 that is at the intersection of the BBL 602 and the upper CCT limit 930. Tie lines 1728, 1738 extend across or through the zone 1020. These tie lines 1728, 1738 may not extend through the zone 1010 shown in FIG. 10. The tie line 1728 intersects the BBL 602 at a color point 1736. Another color point 1734 is beneath the extension of the tie line 1728 (e.g., beyond the BBL 602) and lies on the BBL 602. The color point 1730 represents an intersection of the tie line 1738 with the lower CCT boundary 828 and the color point 1732 represents an extension of the tie line 1738 to a color below the BBL 602, such as at a CCT of 1700 K.

These color points 1730, 1732, 1734, 1736 can represent the outer limits on a range of CCTs and a range of tints (e.g., Duv values) for colors of lights generated by the light source 102 when used in combination with the color point 1720 representing light generated by the light source 104 (e.g., to cause a combination of light from the sources 102, 104 to fall within the zone 1020). The ranges of CCTs and Duv values can be defined in the color space 600 by the portion of the BBL 602 extending from the color point 1736 to the color point 1734, a line extending from the color point 1734 to the color point 1732, a line extending from the color point 1732 to the color point 1730, and a line extending along the lower CCT boundary 828 from the color point 1730 to the color point 1736. A variety of color points falling within the shape defined by the color points 1730, 1732, 1734, 1736 may be used with the color point 1720 to provide a mixed intermediate light falling within the zone 1020.

Figure 18:
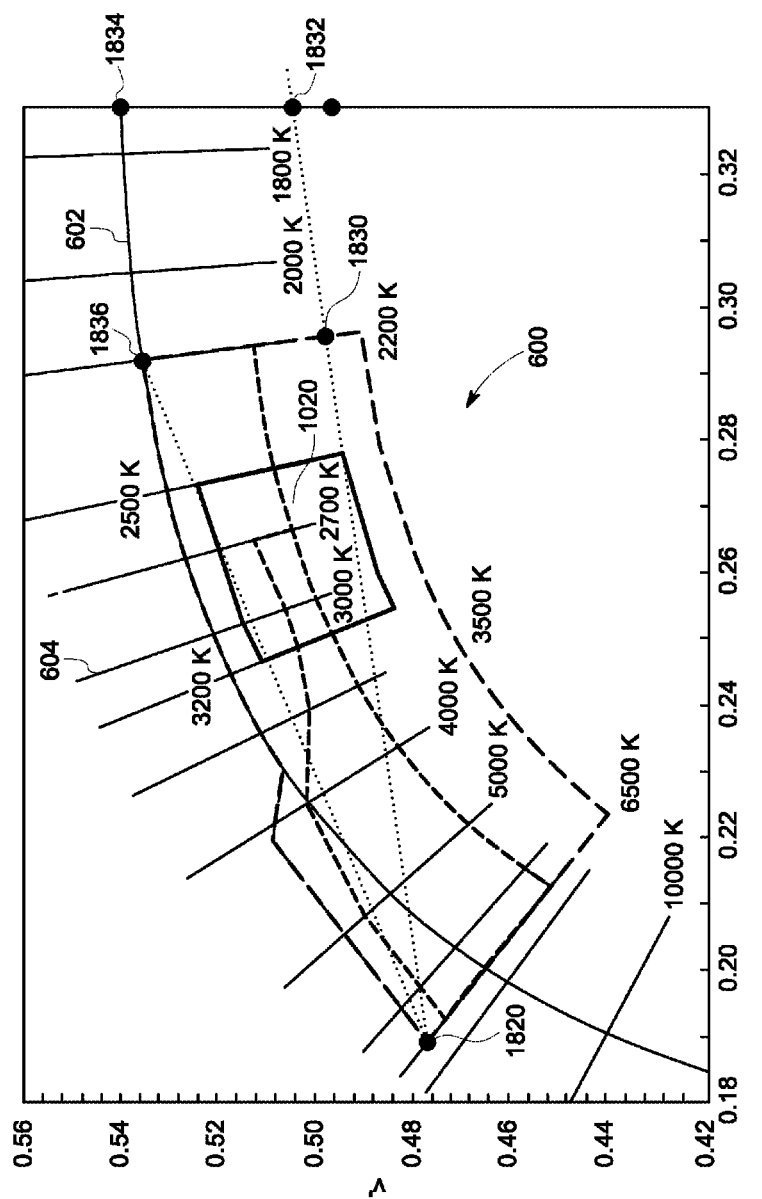
FIG. 18 illustrates additional examples of chromaticities of combinations of light sources shown in FIG. 1a that may be used to generate a warm-white light within the larger, second preferred zone shown in FIG. 10 according to one embodiment.

FIG. 18 illustrates additional examples of combinations of light sources 102, 104 that may be used to generate a warm-white light within the zone 1020 shown in FIG. 10 according to one embodiment. The examples shown in FIG. 18 represent the limits on the color points that may be used for the low-CCT light source 102 when the high-CCT light source 104 has a color point 1820 that is at the intersection of the upper CCT boundary 716, as shown in FIG. 7, and the upper tint limit 712. Tie lines 1838, 1840 extend from the color point 1820 and across or through the zone 1020. These tie lines 1838, 1840 may not extend through the zone 1010 shown in FIG. 10. For example, the tie lines 1838, 1840 may be the outermost tie lines (e.g., the tie lines that are farthest apart while extending from the same color point 1820) that extend over or through the zone 1020.

The tie line 1838 intersects the BBL 602 at a color point 1836. Another color point 1834 is on or beneath the extension of the tie line 1838 (e.g., beyond or above the BBL 602)

and lies on the BBL 602 at a lower CCT. The color point 1830 represents an intersection of the tie line 1840 with the lower CCT boundary 828. The color point 1832 represents an extension of the tie line 1840 to a color point below the BBL 602, such as at a CCT of 1700 K.

These color points 1830, 1832, 1834, 1836 can represent the outer limits on a range of CCTs and a range of tints (e.g., Duv values) for colors of lights generated by the light source 102 when used in combination with the color point 1820 representing light generated by the light source 104 (e.g., to cause a combination of light from the sources 102, 104 to fall within the zone 1020). The ranges of CCTs and Duv values can be defined in the color space 600 by the portion of the BBL 602 extending from the color point 1836 to the color point 1834, a line extending from the color point 1834 to the color point 1832, a line extending from the color point 1832 to the color point 1830, and a line extending along the lower CCT boundary 828 from the color point 1830 to the color point 1836. A variety of color points falling within the shape defined by the color points 1830, 1832, 1834, 1836 may be used with the color point 1820 to provide a mixed intermediate light falling within the zone 1020.

Figure 19:
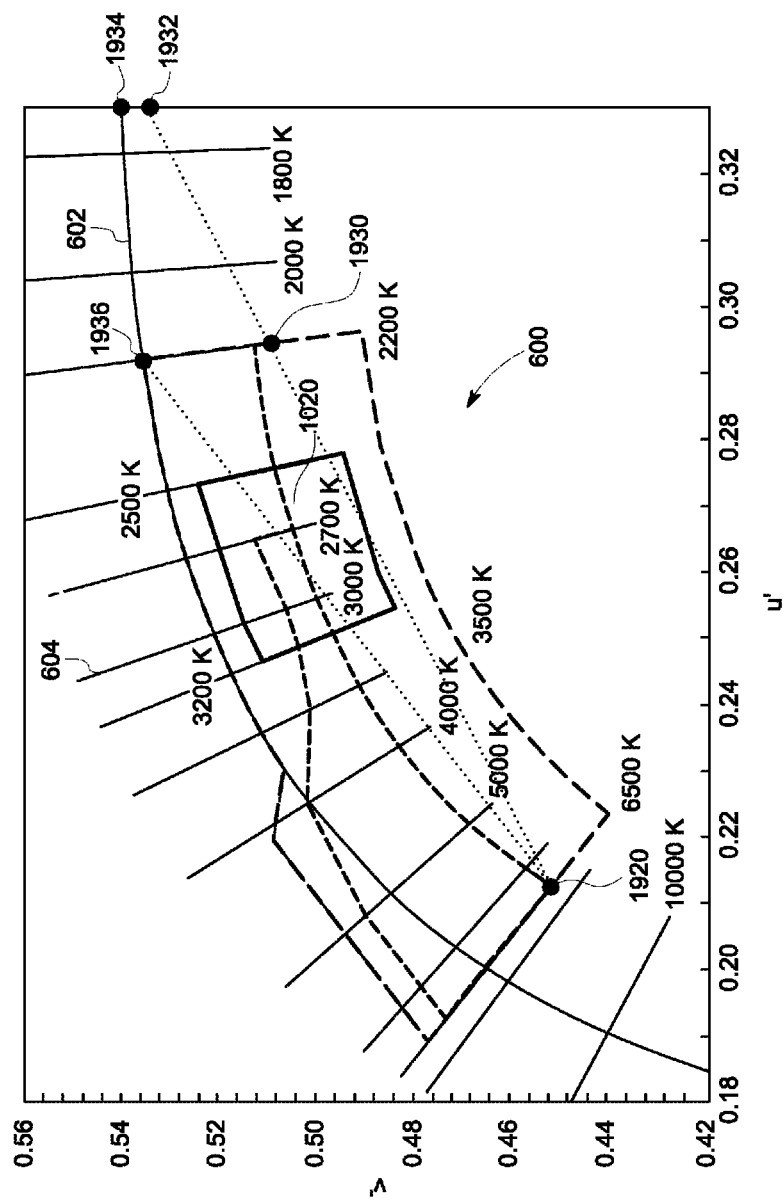
FIG. 19 illustrates additional examples of chromaticities of combinations of light sources shown in FIG. 1a that may be used to generate a warm-white light within the larger, second preferred zone shown in FIG. 10 according to one embodiment.

FIG. 19 illustrates additional examples of combinations of light sources 102, 104 that may be used to generate a warm-white light within the zone 1020 shown in FIG. 10 according to one embodiment. The examples shown in FIG. 19 represent the limits on the color points that may be used for the low-CCT light source 102 when the high-CCT light source 104 has a color point 1920 that is at the intersection of the upper CCT boundary 826 and the preference locus 820. Tie lines 1938, 1940 extend from the color point 1920 and across or through the zone 1020. These tie lines 1938, 1940 may not extend through the zone 1010 shown in FIG. 10. For example, the tie lines 1938, 1940 may be the outermost tie lines (e.g., the tie lines that are farthest apart while extending from the same color point 1920) that extend over or through the zone 1020 while also intersecting the BBL 602 at a CCT that is less than 2500 K.

The tie line 1938 intersects the BBL 602 at a color point 1936. Another color point 1934 is on or beneath the extension of the tie line 1938 (e.g., beyond or above the BBL 602) and lies on the BBL 602 at a lower CCT. The color point 1930 represents an intersection of the tie line 1940 the lower CCT boundary 828. The color point 1932 represents an extension of the tie line 1940 to a color point below the BBL 602, such as at a CCT of 1700 K.

These color points 1930, 1932, 1934, 1936 can represent the outer limits on a range of CCTs and a range of tints (e.g., Duv values) for colors of lights generated by the light source 102 when used in combination with the color point 1920. The ranges of CCTs and Duv values can be defined in the color space 600 by the portion of the BBL 602 extending from the color point 1936 to the color point 1934, a line extending from the color point 1934 to the color point 1932, a line extending from the color point 1932 to the color point 1930, and a line extending along the lower CCT boundary 828 from the color point 1930 to the color point 1936. A variety of color points falling within the shape defined by the color points 1930, 1932, 1934, 1936 may be used with the color point 1920 to provide a light falling within the zone 1020.

Figure 20:
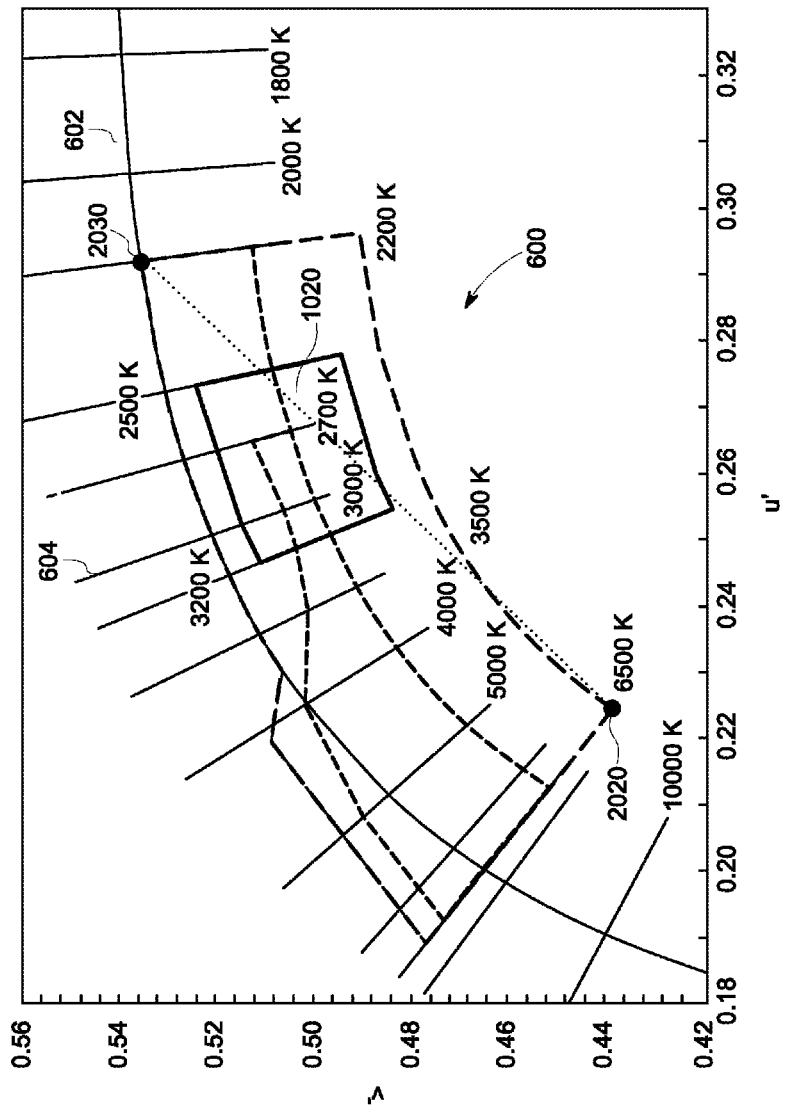
FIG. 20 illustrates an additional example of chromaticities of a combination of light sources shown in FIG. 1a that may be used to generate a warm-white light within the larger, second preferred zone shown in FIG. 10 according to one embodiment.

FIG. 20 illustrates an additional example of a combination of light sources 102, 104 that may be used to generate a warm-white light within the zone 1020 shown in FIG. 10 according to one embodiment. The example shown in FIG. 20 represents color points that may be used for the low-CCT light source 102 when the high-CCT light source 104 has a color point 2020 that is at the intersection of the upper CCT boundary 826 and the lower tint limit 824. A tie line 2032 extends from the color point 2020 and across or through the zone 1020. The tie line 2032 intersects the BBL 602 at a color point 2030, which also lies at the intersection of the BBL 602 and the lower CCT limit 828. The light sources 102, 104 can generate lights having the color points 2020, 2030 to create a combined light having a color that falls within the CCTs and Duv values defined by the zone 1020.

Figure 21:
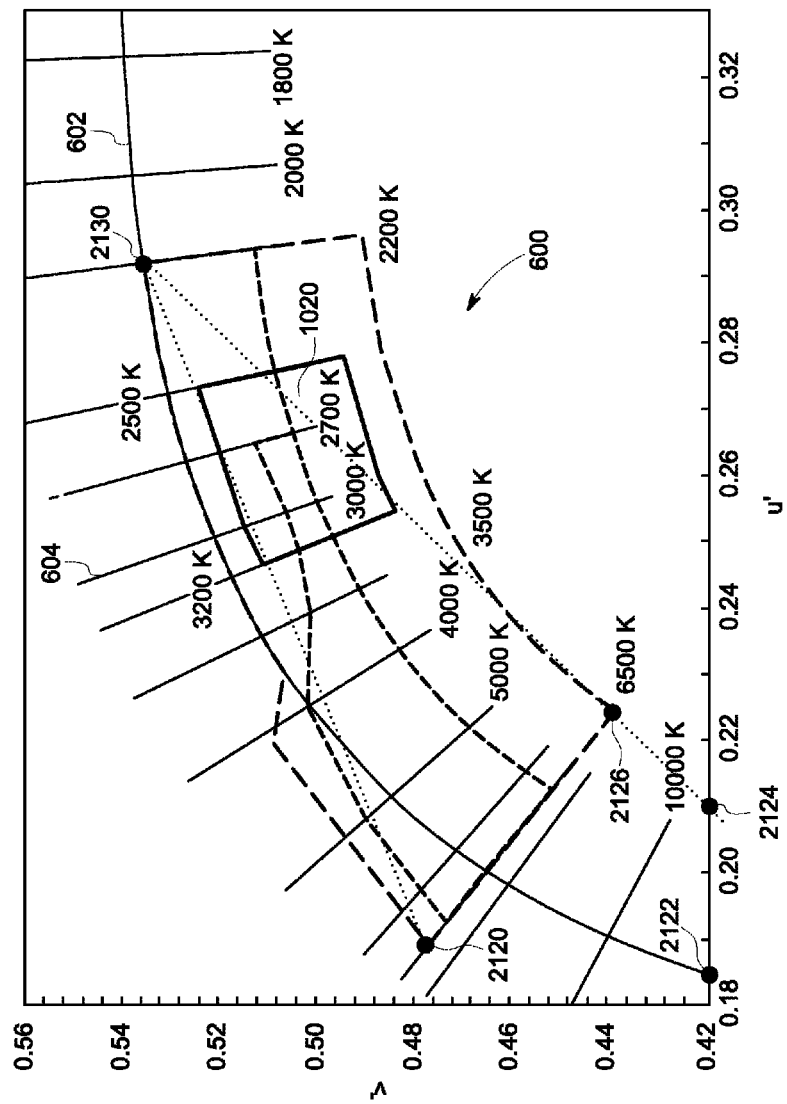
FIG. 21 illustrates additional examples of chromaticities of combinations of light sources shown in FIG. 1a that may be used to generate a warm-white light within the larger, second preferred zone shown in FIG. 10 according to one embodiment.

FIG. 21 illustrates additional examples of combinations of light sources 102, 104 that may be used to generate a warm-white light within the zone 1020 shown in FIG. 10 according to one embodiment. The examples shown in FIG. 21 represent the limits on the color points that may be used for the high-CCT light source 104 when the low-CCT light source 102 has a color point 2130 that is at the intersection of the lower CCT boundary 828 and the BBL 602. Tie lines 2132, 2134 extend from the color point 2130 and across or through the zone 1020. The tie lines 2132, 2134 may be the outermost tie lines (e.g., the tie lines that are farthest apart while extending from the same color point 2130) that extend over or through the zone 1020 while also intersecting the upper CCT limit 930 at 6500K.

The tie line 2132 intersects the upper CCT limit 930 at a color point 2120. Another color point 2122 is on or beneath the extension of the tie line 2132 (e.g., beyond or above the BBL 602) and lies on the BBL 602 at a greater CCT. The color point 2126 represents an intersection of the tie line 2134 with the upper CCT boundary 930. The color point 2124 represents an extension of the tie line 2134 to a color point below the BBL 602, such as at a CCT of 10000 K.

These color points 2120, 2122, 2124, 2126 can represent the outer limits on a range of CCTs and a range of tints (e.g., Duv values) for colors of lights generated by the light source 104 when used in combination with the color point 2130. The ranges of CCTs and Duv values can be defined in the color space 600 by a line extending from the color point 2120 to the color point 2122, a line extending from the color point 2122 to the color point 2124, a line extending from the color point 2124 to the color point 2126, and a line extending along the upper CCT boundary 930 from the color point 2126 to the color point 2120. A variety of color points falling within the shape defined by the color points 2120, 2122, 2124, 2126 may be used with the color point 2130 to provide a mixed intermediate light falling within the zone 1020.

Figure 22:
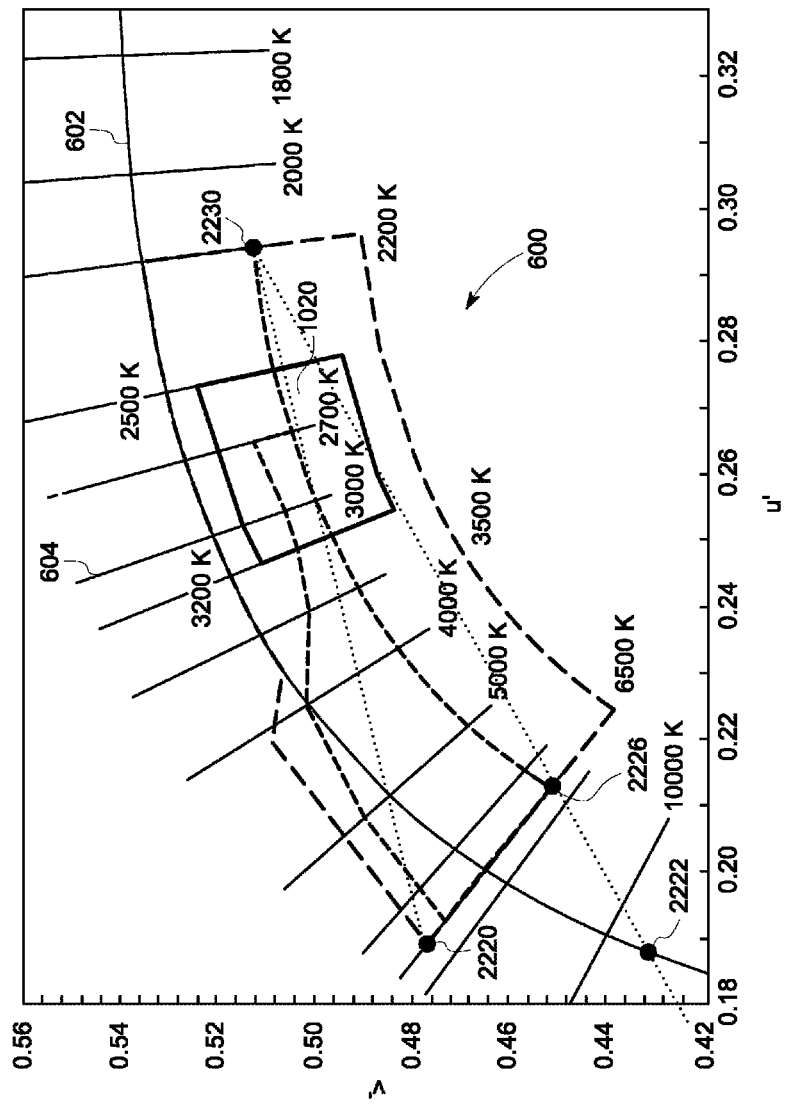
FIG. 22 illustrates additional examples of chromaticities of combinations of light sources shown in FIG. 1a that may be used to generate a warm-white light within the larger, second preferred zone shown in FIG. 10 according to one embodiment.

FIG. 22 illustrates additional examples of combinations of light sources 102, 104 that may be used to generate a warm-white light within the zone 1020 shown in FIG. 10 according to one embodiment. The examples shown in FIG. 22 represent the limits on the color points that may be used for the high-CCT light source 104 when the low-CCT light source 102 has a color point 2230 that is at the intersection of the lower CCT boundary 828 and the preference locus 820. Tie lines 2228, 2232 extend from the color point 2230 and across or through the zone 1020. The tie lines 2228, 2232 may be the outermost tie lines (e.g., the tie lines that are farthest apart while extending from the same color point 2230) that extend over or through the zone 1020 while also intersecting the upper CCT limit 930. The tie line 2228 intersects the upper CCT limit 930 at a color point 2220. The color point 2226 represents an intersection of the tie line 2232 with the upper CCT boundary 930. The color point 2222 represents an extension of the tie line 2232 to the BBL 602.

These color points 2220, 2222, 2224 can represent the outer limits on a range of CCTs and a range of tints (e.g., Duv values) for colors of lights generated by the light source 104 when used in combination with the color point 2230. The ranges of CCTs and Duv values can be defined in the color space 600 by a line extending from the color point 2220 to the color point 2222, a line extending from the color point 2222 to the color point 2226, and a line extending along the upper CCT boundary 930 from the color point 2226 to the color point 2220. A variety of color points falling within the shape defined by the color points 2220, 2222, 2224 may be used with the color point 2230 to provide a mixed intermediate light falling within the zone 1020.

Figure 23:
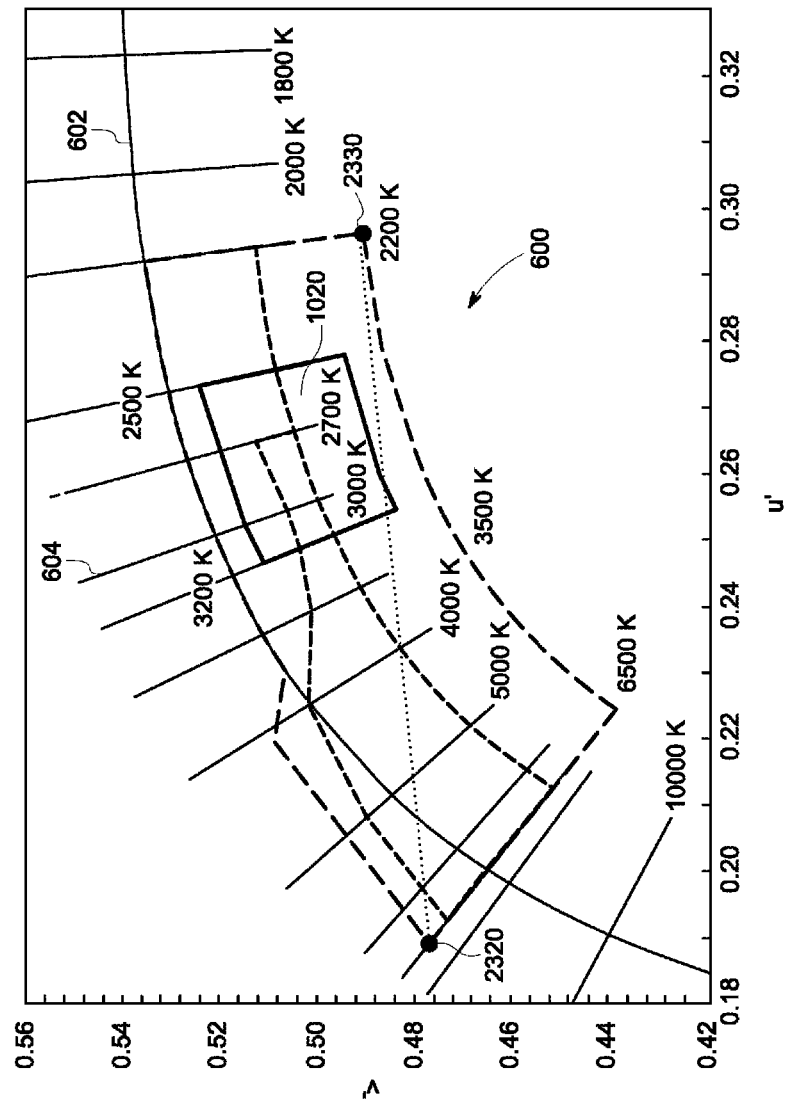
FIG. 23 illustrates an additional example of chromaticities of a combination of light sources shown in FIG. 1a that may be used to generate a warm-white light within the larger, second preferred zone shown in FIG. 10 according to one embodiment.

FIG. 23 illustrates an additional example of a combination of light sources 102, 104 that may be used to generate a warm-white light within the zone 1020 shown in FIG. 10 according to one embodiment. The example shown in FIG. 23 represents a color point that may be used for the high-CCT light source 104 when the low-CCT light source 102 has a color point 2330 that is at the intersection of the lower CCT boundary 828 and the lower tint limit 824. A tie line 2322 extends from the color point 2330 and across or through the zone 1020. The tie line 2322 intersects the upper CCT limit 930 (and the upper tint limit 712) at a color point 2320. The light sources 102, 104 can generate lights having the color points 2330, 2320 to create a combined light having a color that falls within the CCTs and Duv values defined by the zone 1020.

Since the upper and lower boundaries of the zone 1020 might be expected to be slightly higher or lower in the Duv direction, but not as high or low as the upper and lower limits of zone 1030, it can be generalized that the color point in the warm-white CCT range of 2500 K to 3200 K is preferred when the high-blue light source 104 at about 6500 K or higher lies within a Duv range of about 0.015 above the BBL to about 0.030 below the BBL, combined with a low-blue light source 102 at about 2200K or lower that lies within a Duv range of about 0.005 above the BBL to about 0.030 below the BBL.

Figure 24:
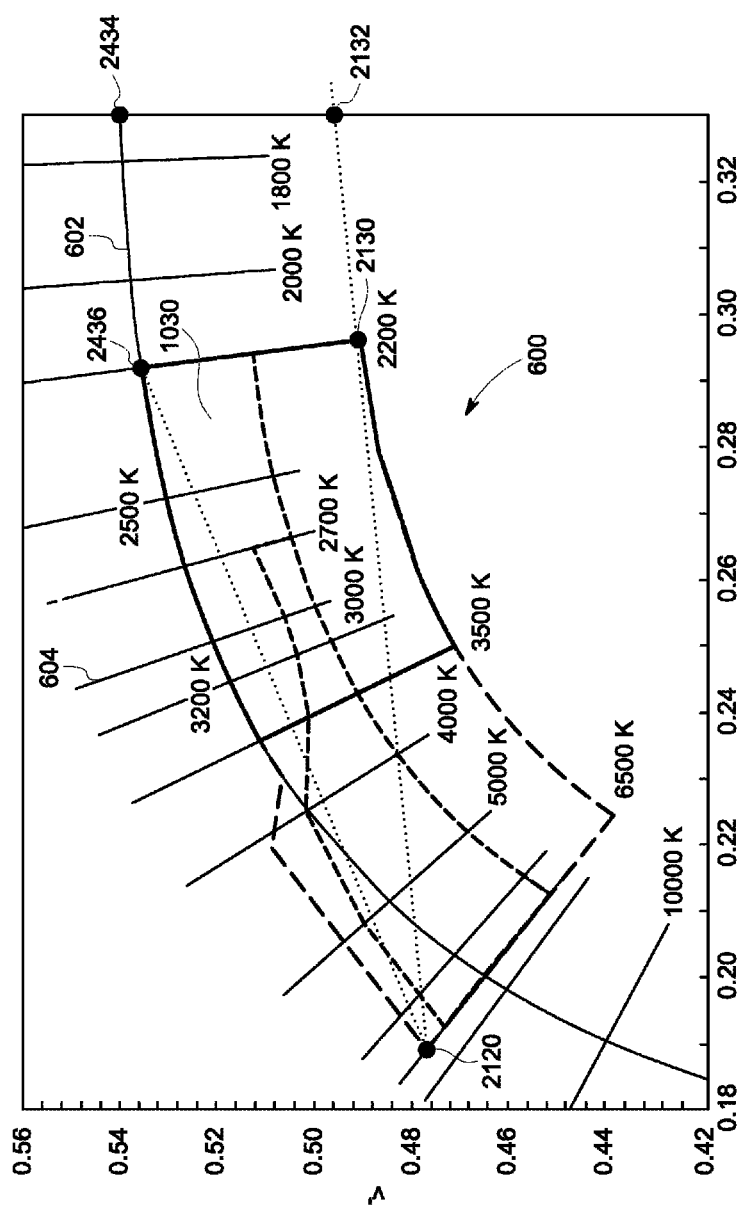
FIG. 24 illustrates examples of chromaticities of combinations of light sources shown in FIG. 1a that may be used to generate a warm-white light within a larger, third preferred zone shown in FIG. 10 according to one embodiment.

FIG. 24 illustrates additional examples of combinations of light sources 102, 104 that may be used to generate a warm-white light within the zone 1030 shown in FIG. 10 according to one embodiment. The examples shown in FIG. 24 represent the limits on the color points that may be used for the low-CCT light source 102 when the high-CCT light source 104 has a color point 2420 that is at the intersection of the upper CCT boundary 930, as shown in FIG. 9, and the upper tint limit 712. Tie lines 2438, 2440 extend from the color point 2420 and across or through the zone 1030. The tie lines 2438, 2440 may be the outermost tie lines (e.g., the tie lines that are farthest apart while extending from the same color point 2420) that extend over or through the zone 1030 while also intersecting the BBL 602 and/or the lower CCT limit 828.

The tie line 2438 intersects the BBL 602 and the lower CCT limit 828 at a color point 2436. Another color point 2434 is on or beneath the extension of the tie line 2438 (e.g., beyond or above the BBL 602) and lies on the BBL 602 at a lower CCT. The color point 2430 represents an intersection of the tie line 2440 with the lower tint limit 824 and/or the lower CCT boundary 828. The color point 2432 represents an extension of the tie line 2440 to a color point below the BBL 602, such as at a CCT of 1700 K.

These color points 2430, 2432, 2434, 2436 can represent the outer limits on a range of CCTs and a range of tints (e.g., Duv values) for colors of lights generated by the light source 102 when used in combination with the color point 2420. The ranges of CCTs and Duv values can be defined in the color space 600 by a line extending from the color point 2436 to the color point 2434 along the BBL 602, a line extending from the color point 2434 to the color point 2432, a line extending from the color point 2432 to the color point 2430, and a line extending along the lower CCT boundary 828 from the color point 2430 to the color point 2436. A variety of color points falling within the shape defined by the color points 2430, 2432, 2434, 2436 may be used with the color point 2420 to provide a mixed intermediate light falling within the zone 1030.

Figure 25:
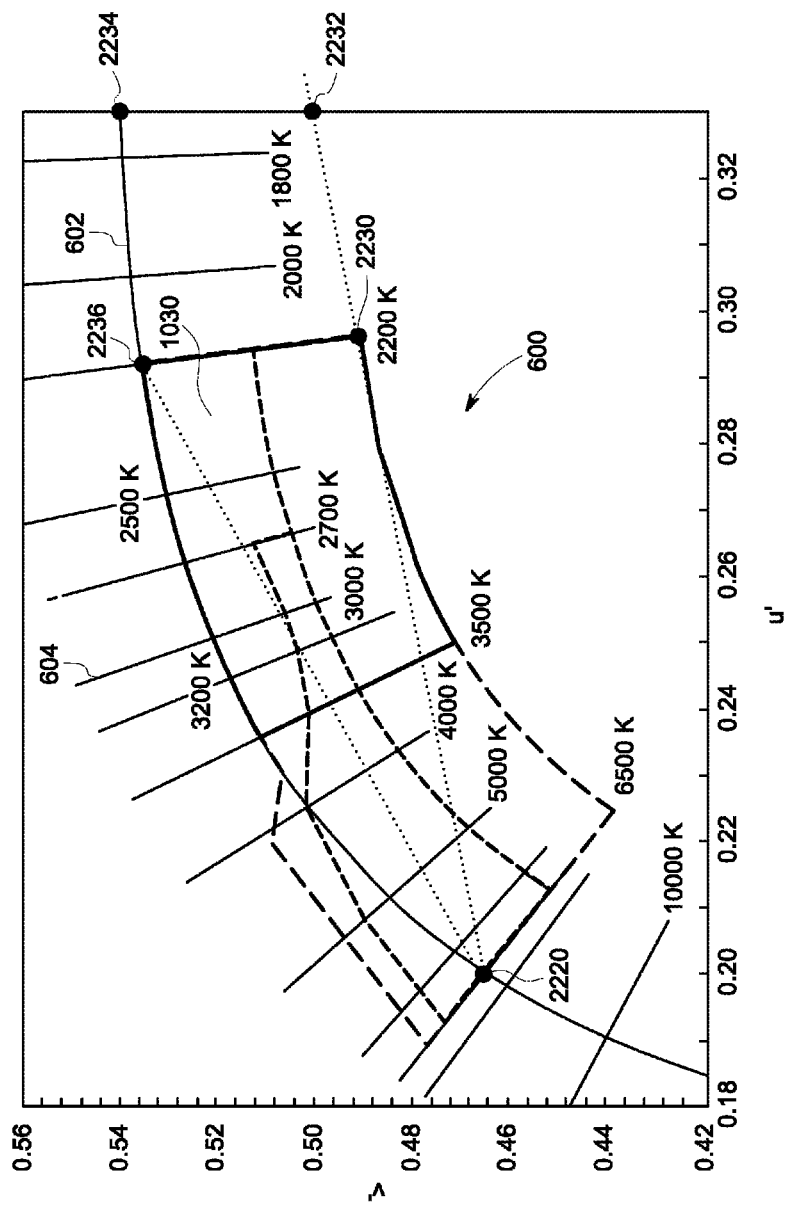
FIG. 25 illustrates additional examples of chromaticities of combinations of light sources shown in FIG. 1a that may be used to generate a warm-white light within the larger, third preferred zone shown in FIG. 10 according to one embodiment.

FIG. 25 illustrates additional examples of combinations of light sources 102, 104 that may be used to generate a warm-white light within the zone 1030 shown in FIG. 10 according to one embodiment. The examples shown in FIG. 25 represent the limits on the color points that may be used for the low-CCT light source 102 when the high-CCT light source 104 has a color point 2520 that is at the intersection of the upper CCT boundary 930 and the BBL 602. Tie lines 2538, 2540 extend from the color point 2520 and across or through the zone 1030. The tie lines 2538, 2540 may be the outermost tie lines (e.g., the tie lines that are farthest apart while extending from the same color point 2520) that extend over or through the zone 1030 while also intersecting the BBL 602, the lower CCT limit 828, and/or the lower tint limit 824.

The tie line 2538 intersects the BBL 602 at a color point 2536. Another color point 2534 is on or beneath the extension of the tie line 2538 (e.g., beyond or above the BBL 602) and lies on the BBL 602 at a lower CCT (e.g., 1700 K). The color point 2530 represents an intersection of the tie line 2540 with the lower tint limit 824 and/or the lower CCT boundary 828. The color point 2532 represents an extension of the tie line 2540 to a color point below the BBL 602, such as at a CCT of 1700 K.

These color points 2530, 2532, 2534, 2536 can represent the outer limits on a range of CCTs and a range of tints (e.g., Duv values) for colors of lights generated by the light source 102 when used in combination with the color point 2520. The ranges of CCTs and Duv values can be defined in the color space 600 by a line extending from the color point 2536 to the color point 2534 along the BBL 602, a line extending from the color point 2534 to the color point 2532, a line extending from the color point 2532 to the color point 2530, and a line extending along the lower CCT boundary 828 from the color point 2530 to the color point 2536. A variety of color points falling within the shape defined by the color points 2530, 2532, 2534, 2536 may be used with the color point 2520 to provide a mixed intermediate light falling within the zone 1030.

Figure 26:
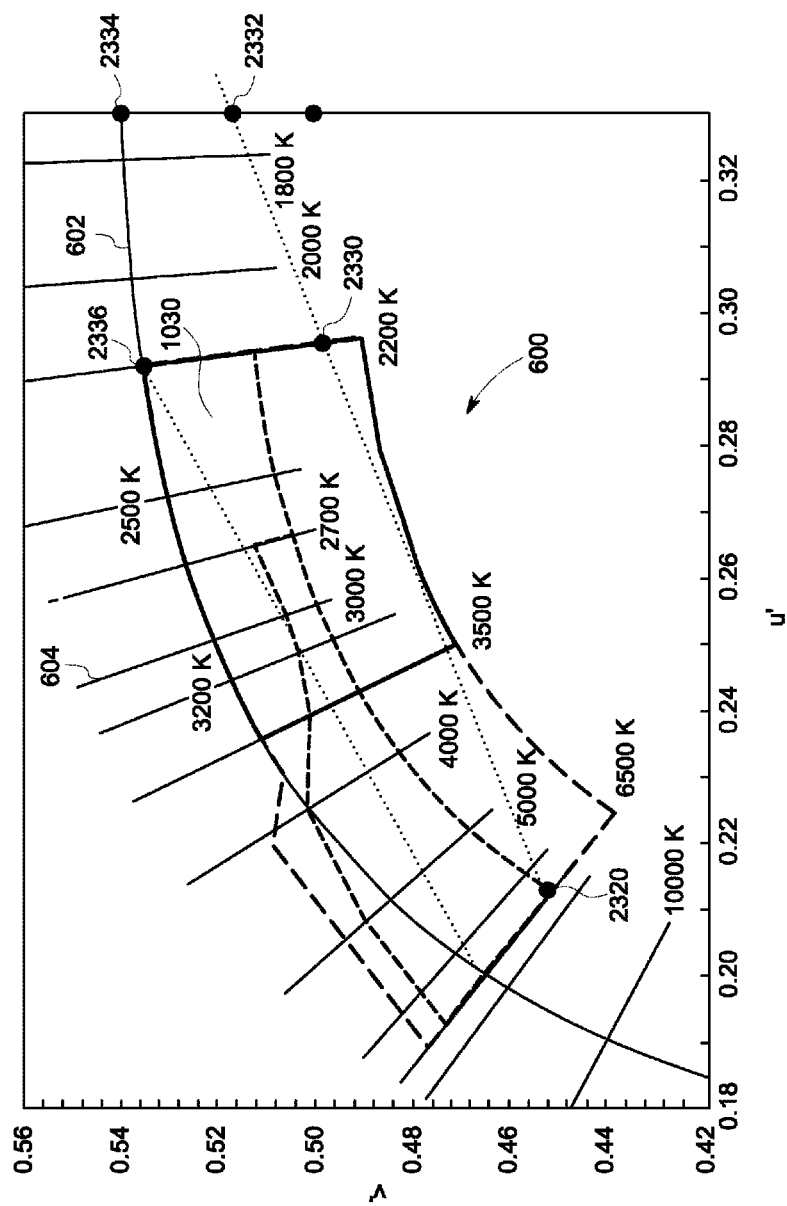
FIG. 26 illustrates additional examples of chromaticities of combinations of light sources shown in FIG. 1a that may be used to generate a warm-white light within the larger, third preferred zone shown in FIG. 10 according to one embodiment.

FIG. 26 illustrates additional examples of combinations of light sources 102, 104 that may be used to generate a warm-white light within the zone 1030 shown in FIG. 10 according to one embodiment. The examples shown in FIG. 26 represent the limits on the color points that may be used for the low-CCT light source 102 when the high-CCT light source 104 has a color point 2620 that is at the intersection of the upper CCT boundary 930 and the preference locus 820. Tie lines 2638, 2640 extend from the color point 2620 and across or through the zone 1030. The tie lines 2638, 2640 may be the outermost tie lines (e.g., the tie lines that are farthest apart while extending from the same color point 2620) that extend over or through the zone 1030 while also intersecting the BBL 602 and/or the lower CCT limit 828.

The tie line 2638 intersects the BBL 602 and the lower CCT limit 828 at a color point 2636. Another color point 2634 is on or beneath the extension of the tie line 2638 (e.g., beyond or above the BBL 602) and lies on the BBL 602 at a lower CCT (e.g., 1700 K). The color point 2630 represents an intersection of the tie line 2640 with the lower CCT limit

828. The color point 2632 represents an extension of the tie line 2640 to a color point below the BBL 602, such as at a CCT of 1700 K.

These color points 2630, 2632, 2634, 2636 can represent the outer limits on a range of CCTs and a range of tints (e.g., Duv values) for colors of lights generated by the light source 102 when used in combination with the color point 2620. The ranges of CCTs and tints can be defined in the color space 600 by a line extending from the color point 2636 to the color point 2634 along the BBL 602, a line extending from the color point 2634 to the color point 2632, a line extending from the color point 2632 to the color point 2630, and a line extending along the lower CCT boundary 828 from the color point 2630 to the color point 2636. A variety of color points falling within the shape defined by the color points 2630, 2632, 2634, 2636 may be used with the color point 2620 to provide a mixed intermediate light falling within the zone 1030.

Figure 27:
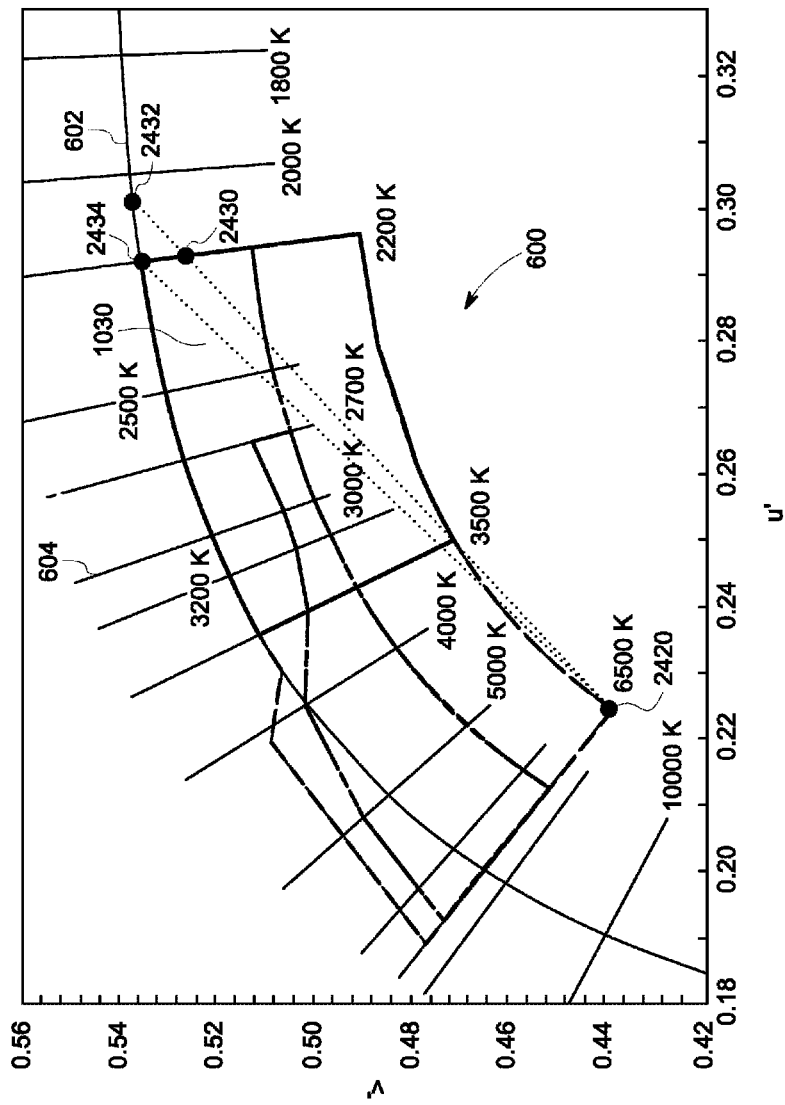
FIG. 27 illustrates additional examples of chromaticities of combinations of light sources shown in FIG. 1a that may be used to generate a warm-white light within the larger, third preferred zone shown in FIG. 10 according to one embodiment.

FIG. 27 illustrates additional examples of combinations of light sources 102, 104 that may be used to generate a warm-white light within the zone 1030 shown in FIG. 10 according to one embodiment. The examples shown in FIG. 27 represent the limits on the color points that may be used for the low-CCT light source 102 when the high-CCT light source 104 has a color point 2720 that is at the intersection of the upper CCT boundary 930 and the lower tint limit 824, as shown in FIG. 8. Tie lines 2736, 2738 extend from the color point 2720 and across or through the zone 1030. The tie lines 2736, 2738 may be the outermost tie lines (e.g., the tie lines that are farthest apart while extending from the same color point 2720) that extend over or through the zone 1030 while also intersecting the BBL 602 and/or the lower CCT limit 828.

The tie line 2736 intersects the BBL 602 and the lower CCT limit 828 at a color point 2734. The tie line 2738 intersects the BBL 602 at a color point 2732 and intersects the lower CCT limit 828 at a color point 2730. These color points 2730, 2732, 2734 can represent the outer limits on a range of CCTs and a range of tints (e.g., Duv values) for colors of lights generated by the light source 102 when used in combination with the color point 2720. The ranges of CCTs and Duv values can be defined in the color space 600 by a line extending from the color point 2734 to the color point 2732 along the BBL 602, a line extending from the color point 2732 to the color point 2730 (e.g., along the tie line 2738), and a line extending from the color point 2730 to the color point 2734 along the lower CCT boundary 828. A variety of color points falling within the shape defined by the color points 2730, 2732, 2734 may be used with the color point 2720 to provide a mixed intermediate light falling within the zone 1030.

Figure 28:
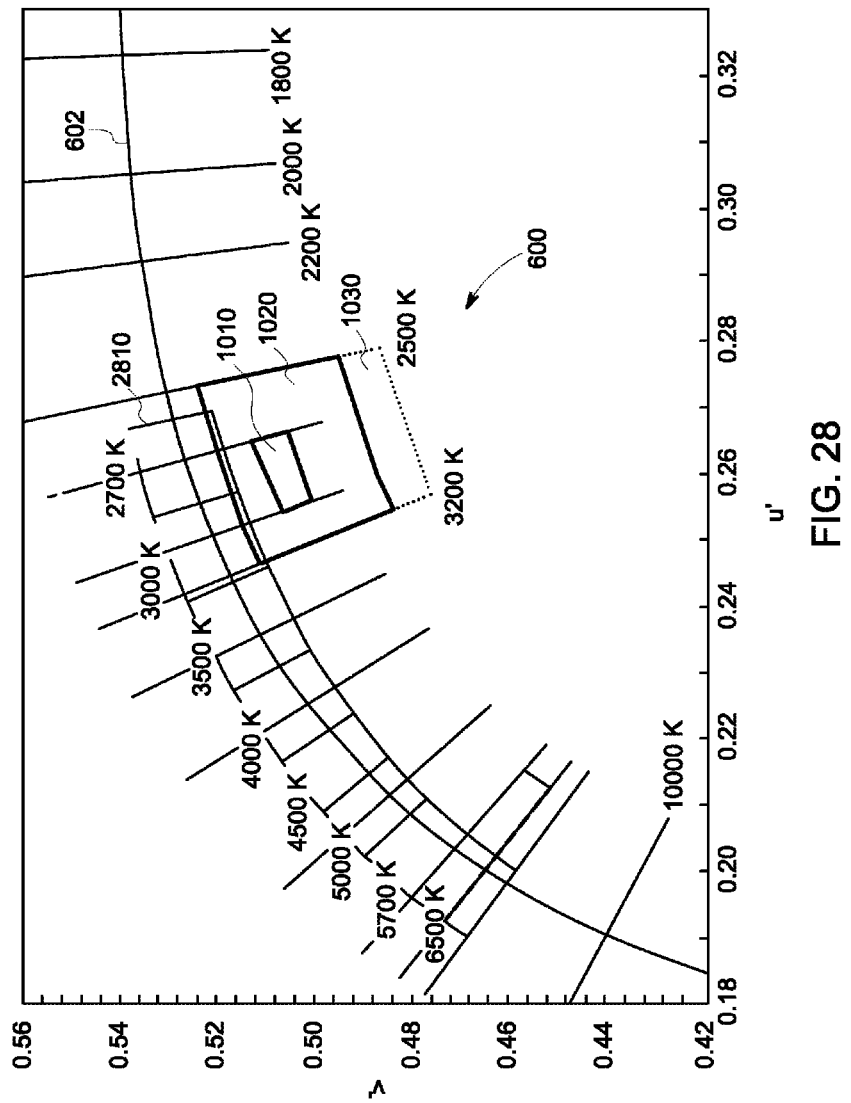
FIG. 28 illustrates the ranges of chromaticities recommended by ANSI Standard C78.377-2011 (American National Standard for Electric Lamps—Specifications for the Chromaticity of Solid State Lighting (SSL) Products) for general lighting (i.e., white light) with SSL products.

FIG. 28 illustrates the ranges of chromaticities recommended by ANSI Standard C78.377-2011 (American National Standard for Electric Lamps—Specifications for the Chromaticity of Solid State Lighting (SSL) Products) for general lighting (i.e., white light) with SSL products. The recommended quadrangles 2810 are approximately centered on the BBL in the Duv direction, and on the CCT isothermal lines. The recently revised ANSI Standard 078.377-2015 also includes similar quadrangles centered on 2500 K and 2200 K. It can be seen from FIG. 28 that the most preferred zone 1010 is not included in the ANSI quadrangles that are recommended for general "white light" applications, and yet the recent color science (2010 Rea, 2013 Freysinnier, 2015 Ohno) indicates that the range of most preferred chromaticity 1010 in FIG. 28 is not included in any of the ANSI quadrangles, and that nearly all of the more preferred chromaticity range 1020 in FIG. 28 is not included in any of the ANSI quadrangles.

Existing lighting systems that provide for low-CCT and high-CCT color points, as well as a color point at an intermediate CCT generally provide for a third light source at, or near, the intermediate CCT which is on or near the BBL so that the color points of all possible intermediate CCTs created by mixing the three light sources may be located on or near the BBL. In this invention, the elimination of the third light source at the intermediate CCT not only simplifies the lighting system, but also provides a more preferred color point at a warm-white intermediate CCT, and may even provide the most preferred color point.

Returning to the description of the lamp system 100 shown in FIG. 1, the lamp system 100 may operate by the low-blue component light source 102 emitting substantially white light and the high-blue component light source 104 emitting substantially white light. The substantially white light generated by the light source 104 can have a greater correlated color temperature (CCT) than the substantially white light generated by the light source 102. The substantially white lights generated by the light sources 102, 104 can combine to provide substantially intermediate or warm-white light emanating from the lamp system 100. The low-blue component light source 102 can emit the substantially white light to have a CCT of no greater than about 2500 K. This light may be produced to have a CCT of at least 2000 K in one embodiment. The high-blue component light source 104 can emit the substantially white light to have a CCT of at least about 4000 K. This light may be generated to have a CCT of no more than 10,000 K in one embodiment. The intermediate or warm-white light emanating from the lamp system 100 can have a CCT of at least about 2700 K and no greater than about 3000 K in one embodiment.

The lamp system 100 can include an optical system 114 through which the light generated by the light sources 102, 104 propagate and substantially uniformly mix before emanating from the lamp system 100. The optical system 114 may include or represent a lens formed from light transmissive material, such as a polymer, glass, or the like; or light reflective material such as metal, or polymer or any reflectively coating on a substrate; or a combination of light transmissive and light reflective elements. The optical system 114 may scatter, diffract, refract, reflect, diffuse, or otherwise mix the lights generated by the light sources 102, 104 when both light sources 102, 104 generate light.

The lamp system 100 includes a switch 116 that controls which of the light sources 102, 104 generate light. The switch 116 can alternate between different states or positions to activate the different light sources 102, 104, such as by controlling which light source 102, 104 receives electric current to power the light sources 102, 104 from a power source (e.g., an outlet, utility grid, battery, or the like). In one state, the switch 116 causes the low-blue component light source 102 to emit light while the high-blue component light source 104 does not emit light. This state can be used by an operator of the lamp system 100 to cause the lamp system 100 to generate light that does not suppress or encourages melatonin generation in the human body, so as to help a human being fall asleep. In a different state, the switch 116 causes the low-blue component light source 102 to not emit light while the high-blue component light source 104 emits light. This state can be used by an operator of the lamp system 100 to cause the lamp system 100 to generate light that suppresses melatonin generation in the human body, so as to help a human wake up. In one embodiment, the switch 116 causes the low-blue component light source 102 to emit light while the high-blue component light source 104 also emits light to provide the substantially intermediate or warm-white light. This state can allow for the lamp system 100 to be used during times when the operator does not wish to suppress or stop suppression of melatonin generation, such as during time periods throughout the day when the operator is not trying to wake up or fall asleep. The switch 116 can be a device that can be manually actuated in order to change operational states of the lamp system 100.

In one aspect, the lamp system 100 includes a timer 118 that controls which of the low-blue component light source 102 and the high-blue component light source 104 is activated at different times. The timer 118 can represent hardware circuitry that tracks passage of time, such as an electronic clock. The timer 118 can include and/or have access to a memory that stores times at which the different light sources 102, 104 are to be activated or deactivated. Based on the stored times, the timer 118 can control the light sources 102, 104 and/or the switch 116 to cause the low-blue component light source 102 to emit light and deactivate the high-blue component light source 104 during a pre-sleep time period, such as between 8 pm and midnight (or other times). The timer 118 can control the light sources 102, 104 and/or the switch 116 to activate the high-blue component light source 104 to emit light and deactivate the low-blue component light source 102 during a post-sleep time period, such as between 5 am and 9 am (or other times). The timer 118 can activate both the low-blue component light source 102 and the high-blue component light source 104 during a time period subsequent to the post-sleep time period and prior to the pre-sleep time period, such as between 9 am and 8 pm, or other time periods. This can allow for the lamp system 100 to switch between which lights are being produced at different times to avoid having the operator make manual adjustments, such as by removing or replacing light sources during different times.

In the illustrated embodiment, the lamp system 100 includes a control unit 120. The control unit 120 represents hardware circuitry that includes and/or is connected with one or more processors, such as field programmable gate arrays (FPGAs), integrated circuits, microprocessors, or other electronic logic-based devices. The control unit 120 can be used to program the timer 118 (e.g., to set the time, set the times at which the different light sources 102, 104 are activated or deactivated, etc.). The control unit 120 optionally may control the timer 118 and/or switch 116 in order to automatically (e.g., without operator intervention) switch which light source 102, 104 is activated at different times of the day. In one embodiment, the control unit 120, switch 116, and/or timer 118 can be a separate component from the light sources 102, 104. For example, the light sources 102, 104 and/or lens 114 may be a separately purchasable component that can be detachably coupled with the control unit 120, switch 116, and/or timer 118. The light sources 102, 104 can be replaced when one or more of the light sources 102, 104 burns out or is otherwise unable to produce light.

Certain advantages may be presented by embodiments of this disclosure. For example, embodiments of this disclosure may provide a composite light source that can serve as "high-blue" light in the morning to feel alert, a spectrally enhanced intermediate or warm-white light throughout the day for regular tasks, and as a "low-blue" light in the evening to assist in sleep.

Although certain embodiments are described above with respect to the color point of the composite light source (arrived at by pointing to a certain color point on a tie line), it should be understood that different color points for the low-blue and high-blue component light sources, will result in different tie lines and intermediate or warm-white color points; and yet, all of the foregoing should be considered as subsumed into the scope of this disclosure. Although certain embodiments are described above that employ PFS red phosphor, one of ordinary skill in the art would understood that an alternative narrow red phosphor, and/or red LED, and/or other narrow red emitter could be used in place of PFS for enhanced color quality and efficacy. It should also be understood that although certain exemplary embodiments provide a composite light source that is a combination of two "channels" (e.g., two component light sources, with one being high-blue and one being low-blue), the disclosure is not limited to this; a multi-channel solution (greater than or equal to three component light sources) could be employed to achieve various color points and effects.

While certain Duv values are provided for different lights having different CCTs, optionally, these lights may have other Duv values. For example, the light having a CCT of at least 4000K, or at least another value like 6000K, may have a Duv value from −0.030 to +0.015, a Duv value that is greater than −0.015 and no greater than +0.015, or another value. The light having a CCT of 2200K or lower may have a Duv value from −0.030 to +0.005, a Duv value that is less than 0.000 and no less than −0.015, or another value.

In one embodiment, a composite light source includes a low-blue component light source emitting first substantially white light and a high-blue component light source emitting second substantially white light. The second substantially white light has a greater correlated color temperature than the first substantially white light. The first and second substantially white light combine to provide substantially intermediate or warm-white light.

In one aspect, the low-blue component light source emits the first substantially white light comprising a correlated color temperature of no greater than about 2500 K.

In one aspect, the high-blue component light source emits the second substantially white light comprising a correlated color temperature of at least about 4000 K.

In one aspect, the intermediate or warm-white light has a correlated color temperature of at least about 2700 K and no greater than about 3000K.

In one aspect, the composite light source also includes a switch configured to be actuated to a first state to cause the low-blue component light source to emit the first substantially white light while the high-blue component light source does not emit the second substantially white light. The switch also is configured to be actuated to a different, second state to cause the low-blue component light source to not emit the first substantially white light while the high-blue component light source does emit the second substantially white light. The switch also is configured to be actuated to a different, third state to cause the low-blue component light source to emit the first substantially white light while the high-blue component light source emits the second substantially white light to provide the substantially intermediate or warm-white light.

In one aspect, the composite light source also includes a timer that controls which of the low-blue component light source and the high-blue component light source is activated at different times of a day.

In one aspect, the timer activates the low-blue component light source to emit the first substantially white light and deactivates the high-blue component light source during a pre-sleep time period. The timer can activate the high-blue component light source to emit the second substantially white light and deactivates the low-blue component light source during a post-sleep time period. The timer also can activate the low-blue component light source and the high-blue component light source during a time period subsequent to the post-sleep time period and prior to the pre-sleep time period.

In one aspect, at least one of the low-blue component light source or the high-blue component light source comprises a narrow-band red emitter.

In one aspect, the narrow-band red emitter is a phosphor.

In one aspect, the composite light source includes a lens through which both the first and second substantially white light are emitted.

In another embodiment, a method (e.g., for generating light) includes emitting first substantially white light from a low-blue component light source of a composite light source during a first time period and emitting second substantially white light from a high-blue component light source during a different, second time period, where the second substantially white light has a greater correlated color temperature than the first substantially white light.

In one aspect, the method also includes concurrently emitting the first substantially white light and emitting the second substantially white light during a different, third time period, where the first and second substantially white light combine to provide substantially intermediate or warm-white light.

In one aspect, the intermediate or warm-white light has a correlated color temperature of at least about 2700 K and no greater than about 3000 K.

In one aspect, the first substantially white light has a correlated color temperature of no greater than about 2500 K.

In one aspect, the second substantially white light has a correlated color temperature of at least about 4000 K.

In one aspect, the method also includes one or more of switching from emitting the first substantially white light from the low-blue component light source to emitting the second substantially white light from the high-blue component light source responsive to actuation of a switch of the composite light source, switching from emitting the second substantially white light from the high-blue component light source to emitting the first substantially white light from the low-blue component light source responsive to actuation of the switch, and/or switching from emitting only the first substantially white light from the low-blue component light source or emitting only the second substantially white light from the high-blue component light source to concurrently emitting both the first substantially white light from the low-blue component light source and the second substantially white light from the high-blue component light source responsive to actuation of the switch.

In one aspect, the method includes one or more of autonomously switching from emitting the first substantially white light from the low-blue component light source to emitting the second substantially white light from the high-blue component light source based on a time of day, autonomously switching from emitting the second substantially white light from the high-blue component light source to emitting the first substantially white light from the low-blue component light source based on the time of day, and/or autonomously switching from emitting only the first substantially white light from the low-blue component light source or emitting only the second substantially white light from the high-blue component light source to concurrently emitting both the first substantially white light from the low-blue component light source and the second substantially white light from the high-blue component light source responsive to actuation of the switch based on the time of day.

In one aspect, the method also includes activating the low-blue component light source to emit the first substantially white light and deactivating the high-blue component light source during a pre-sleep time period, activating the high-blue component light source to emit the second substantially white light and deactivating the low-blue component light source during a post-sleep time period, and activating the low-blue component light source and the high-blue component light source during a time period subsequent to the post-sleep time period and prior to the pre-sleep time period.

In another embodiment, a composite light source includes a low-blue component light source emitting first substantially white light having a correlated color temperature (CCT) of no greater than about 2500 K, a high-blue component light source emitting second substantially white light having a CCT of at least about 4000 K, and a control unit to control which of the low-blue component light source and the high-blue component light source is activated to emit the respective first substantially white light or the second substantially white light.

In one aspect, the control unit activates the low-blue component light source to emit the first substantially white light and deactivates the high-blue component light source during a pre-sleep time period, activates the high-blue component light source to emit the second substantially white light and deactivates the low-blue component light source during a post-sleep time period, and activates the low-blue component light source and the high-blue component light source during a time period subsequent to the post-sleep time period and prior to the pre-sleep time period.

The foregoing description of certain embodiments of the inventive subject matter will be better understood when read in conjunction with the appended drawings. The various embodiments are not limited to the arrangements and instrumentality shown in the drawings. The above description is illustrative and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Other embodiments may be apparent to one of ordinary skill in the art upon reviewing the above description. The scope of the inventive subject matter should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure. And, as used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A composite light source, comprising:
a low-blue component light source emitting first substantially white light; and
a high-blue component light source emitting second substantially white light, the second substantially white light having a greater correlated color temperature than the first substantially white light, wherein at least one of the low-blue component light source and the high-blue component light source comprises a narrow-band red emitter,
wherein the first and second substantially white light combine to provide a combined substantially white light having an intermediate correlated color temperature, wherein the combined substantially white light comprises a standard red color chip ($R_9$) value of at least 51 and has a correlated color temperature that is at least 2500 K and no more than 3200 K and that has a Duv value of at least −0.025 and no more than −0.005.

2. The composite light source of claim 1, wherein the combined substantially white light has a color correlated temperature that is at least 2700 K and no more than 3000 K and that has a Duv value of at least −0.015 and that lies on or below a white body locus.

3. The composite light source of claim 1, further comprising
a switch configured to be actuated to a first state to cause the low-blue component light source to emit the first substantially white light while the high-blue component light source does not emit the second substantially white light, the switch further configured to be actuated to a different, second state to cause the low-blue component light source to not emit the first substantially white light while the high-blue component light source does emit the second substantially white light, the switch yet further configured to be actuated to a different, third state to cause the low-blue component light source to emit the first substantially white light while the high-blue component light source emits the second substantially white light to provide the combined substantially intermediate light.

4. The composite light source of claim 1, further comprising a timer that controls the ratio and the total light flux of the low-blue component light source and the high-blue component light sources at different times of a day.

5. The composite light source of claim 4, wherein the timer activates the low-blue component light source to emit the first substantially white light and deactivates the high-blue component light source during a pre-sleep time period, the timer activates the high-blue component light source to emit the second substantially white light and deactivates the low-blue component light source during a post-sleep time period, and the timer activates the low-blue component light source and the high-blue component light source during a time period subsequent to the post-sleep time period and prior to the pre-sleep time period.

6. The composite light source of claim 1, wherein the narrow-band red emitter is a phosphor.

7. The composite light source of claim 6, wherein the phosphor is formed from potassium fluoro-silicate.

8. The composite light source of 6, wherein the substantially intermediate light includes one or more of a standard red color chip ($R_9$) value of at least 80, a gamut area index value of at least 80, and a lighting preference index of at least 110.

9. A method comprising:
emitting first substantially white light from a low-blue component light source of a composite light source during a first time period; and
emitting second substantially white light from a high-blue component light source during a different, second time period, the second substantially white light having a greater correlated color temperature than the first substantially white light;
wherein at least one of the low-blue component light source and the high-blue component light source comprises a narrow-band red emitter; and
wherein the method further comprises concurrently emitting the first substantially white light and emitting the second substantially white light during a different, third time period, wherein the first and second substantially white light combine to provide combined substantially intermediate light;
wherein the combined substantially white light has a color correlated temperature that is at least 2500 K and no more than 3200 K and that has a Duv value of at least −0.025 and no more than −0.005.

10. The method of claim 9, wherein the combined substantially white light has a color correlated temperature that is at least 2700 K and no more than 3000 K and that has a Duv value of at least −0.015 and that lies on or below a white body locus.

11. The method of claim 9, further comprising one or more of:
switching from emitting the first substantially white light from the low-blue component light source to emitting the second substantially white light from the high-blue component light source responsive to actuation of a switch of the composite light source;
switching from emitting the second substantially white light from the high-blue component light source to emitting the first substantially white light from the low-blue component light source responsive to actuation of the switch; and
switching from emitting only the first substantially white light from the low-blue component light source or emitting only the second substantially white light from the high-blue component light source to concurrently emitting both the first substantially white light from the low-blue component light source and the second substantially white light from the high-blue component light source responsive to actuation of the switch.

12. The method of claim 9, further comprising one or more of:
   autonomously switching from emitting the first substantially white light from the low-blue component light source to emitting the second substantially white light from the high-blue component light source based on a time of day;
   autonomously switching from emitting the second substantially white light from the high-blue component light source to emitting the first substantially white light from the low-blue component light source based on the time of day; and
   autonomously switching from emitting only the first substantially white light from the low-blue component light source or emitting only the second substantially white light from the high-blue component light source to concurrently emitting both the first substantially white light from the low-blue component light source and the second substantially white light from the high-blue component light source responsive to actuation of the switch based on the time of day.

13. The method of claim 9, further comprising:
   activating the low-blue component light source to emit the first substantially white light and deactivating the high-blue component light source during a pre-sleep time period;
   activating the high-blue component light source to emit the second substantially white light and deactivating the low-blue component light source during a post-sleep time period; and
   activating the low-blue component light source and the high-blue component light source during a time period subsequent to the post-sleep time period and prior to the pre-sleep time period.

14. A composite light source, comprising:
   a low-blue component light source emitting first substantially white light; and
   a high-blue component light source emitting second substantially white light, the second substantially white light having a greater correlated color temperature than the first substantially white light, wherein both the low-blue component light source and the high-blue component light source comprises a narrow-band red phosphor emitter,
   wherein the first and second substantially white light combine to provide a combined substantially white light having an intermediate correlated color temperature with an R9 value of at least 80 and a Duv value of at least −0.025 and no more than −0.005.

* * * * *